(12) United States Patent
Allen et al.

(10) Patent No.: US 6,579,986 B2
(45) Date of Patent: *Jun. 17, 2003

(54) PREPARATION OF QUINOLINE-SUBSTITUTED CARBONATE AND CARBAMATE DERIVATIVES

(75) Inventors: Michael S. Allen, Trevor, WI (US); Ramiya H. Premchandran, Gurnee, IL (US); Sou-Jen Chang, Prairie View, IL (US); Stephen Condon, Kenosha, WI (US); John A. DeMattei, Gurnee, IL (US); Steven A. King, Gurnee, IL (US); Lawrence Kolaczkowski, Gurnee, IL (US); Sukumar Manna, Libertyville, IL (US); Paul J. Nichols, Wildwood, IL (US); Hemant H. Patel, Bodakdev (IN); Subhash R. Patel, Chicago, IL (US); Daniel J. Plata, Wadsworth, IL (US); Eric J. Stoner, Kenosha, WI (US); Jien-Heh J. Tien, Vernon Hills, IL (US); Steven J. Wittenberger, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/134,777

(22) Filed: Apr. 29, 2002

(65) Prior Publication Data

US 2002/0165390 A1 Nov. 7, 2002

Related U.S. Application Data

(62) Division of application No. 09/518,392, filed on Mar. 3, 2000, now Pat. No. 6,417,366.
(60) Provisional application No. 60/141,042, filed on Jun. 24, 1999.

(51) Int. Cl.$^7$ .................. C07D 215/36; C07D 215/38; C07D 215/18; A61K 31/47
(52) U.S. Cl. .................. 546/155; 514/311; 514/312; 514/313; 514/314; 546/159; 546/176; 546/180
(58) Field of Search ................ 514/311, 312, 513/313, 314; 546/155, 159, 176, 180

(56) References Cited

U.S. PATENT DOCUMENTS

| 4,154,834 A | 5/1979 | Brown et al. |
| 4,739,106 A | 4/1988 | Miyano et al. |
| 5,128,448 A | 7/1992 | Danho et al. |
| 5,866,549 A | 2/1999 | Or et al. |
| 5,919,776 A | * 7/1999 | Hagmann et al. ............ 514/159 |
| 5,994,368 A | 11/1999 | Oku et al. |
| 6,417,366 B2 | * 7/2002 | Allen et al. ................. 546/153 |
| 6,437,106 B1 | * 8/2002 | Stoner et al. ................ 536/7.4 |
| 6,455,680 B1 | * 9/2002 | Lukin ......................... 546/7.3 |

FOREIGN PATENT DOCUMENTS

| DE | 25 54 790 | 7/1976 |
| DE | 28 38 701 | 3/1979 |
| EP | 0 216 869 | 11/1987 |
| EP | 0 477 159 | 3/1992 |
| EP | 0 579 102 | 1/1994 |
| EP | 0 628 542 | 12/1994 |
| EP | 0 878 463 | 11/1998 |
| EP | 0 926 138 | 6/1999 |
| EP | 0 974 584 | 1/2000 |
| WO | 95/31438 | 11/1995 |
| WO | 99/02524 | 1/1999 |

OTHER PUBLICATIONS

Beller, A., *Chem. Int. Ed. Engl.*, 34(17):1848 (1995).
Beyer, "Lehrbuch der Organischen Chemie", *S. Hirzel Verlag, Leipzig*, 1968, p. 80 & p. 97.
*Chem. Pharm. Bull.*, 27(1):270–273 (1979).
Greene and Wuts, *Protective Groups in Organic Synthesis*, $2^{nd}$ ed., John Wiley & Son, Inc., (1991).
Heck, et al., *J. Org. Chem.*, 37:2320 (1972).
Meth–Cohn, et al., *J.C.S. perkin I.*, 1520–1530 (1981).
Weast, Ed., "Handbook of Chemistry and Physics", $52^{nd}$ Ed., 1971, p. C–457, C–458 & C–459.

* cited by examiner

*Primary Examiner*—D. Margaret Seaman
(74) *Attorney, Agent, or Firm*—B. Gregory Donner

(57) ABSTRACT

The invention relates to a process for preparing quinoline-substituted carbonate and carbamate compounds, which are important intermediates in the synthesis of 6-O-substituted macrolide antibiotics. The process employs metal-catalyzed coupling reactions to provide a carbonate or carbamate of formula (I) or (II) or a substrate that can be reduced to obtain the same.

5 Claims, No Drawings

PREPARATION OF QUINOLINE-SUBSTITUTED CARBONATE AND CARBAMATE DERIVATIVES

This application is a divisional application of U.S. application Ser. No. 09/518,392 now U.S. Pat. No. 6,417,366, which claims priority from the U.S. Provisional Application serial No. 60/141,042, filed on Jun. 24, 1999.

TECHNICAL FIELD OF THE INVENTION

The present invention relates to the preparation of quinoline-substituted carbonate and carbamate derivatives, which provide important intermediates in the synthesis of 6-O-substituted macrolide antibiotics. In one aspect, the invention relates to the processes for preparing quinolyl-substituted carbonate or carbamate compounds and processes for preparing the compounds via an alkenol derivative. In another aspect, the invention relates to preparing carbonate or carbamate compounds via a quinoline carboxaldehyde or a derivative thereof.

BACKGROUND OF THE INVENTION

6-O-Methylerythromycin A (clarithromycin) is a potent macrolide antibiotic disclosed in U.S. Pat. No. 4,331,803.

The process for making clarithromycin, in general, can be thought of as a four-step procedure beginning with erythromycin A as the starting material:

Step 1: optionally convert the 9-oxo group to an oxime;
Step 2: protect the 2' and 4" hydroxyl groups;
Step 3: methylate the 6-hydroxyl group; and
Step 4: deprotect at the 2', 4" and 9-positions.

Since the discovery of clarithromycin, new macrolide antibiotic compounds have been discovered and are disclosed in commonly-owned U.S. Pat. No. 5,886,549, filed Jul. 3, 1997. The compounds generally are prepared by known processes. However, the substitution at the 6-position with substituents other than the methyl group is not easy to accomplish and is accompanied by side reactions, by-products and low yields.

Recent developments provide more efficient and cleaner syntheses for alkylating the 6-hydroxyl group. Novel processes allow substituents other than the methyl in the 6-position of the erythromycin derivatives. Commonly-owned U.S. Application Ser. No. 60/149,968, filed on Jun. 24, 1999, discloses a process for preparing 6-O-substituted erythromycin derivatives and for preparing 6-O-substituted erythromycin ketolides involving a palladium catalyzed process using carbonate or carbamate derivatives.

Preparation of the carbonate and carbamate derivatives involve use of a variety of quinoline substituted intermediates. In *Chem. Pharm. Bull.*, 1979, 27(1), 270–273, synthesis of 3-(3-quinolyl)-2-propyn-1-ol is described. However, there are no known reports of quinoline substituted carbonate or carbamate derivatives or the methods of preparing them.

SUMMARY OF THE INVENTION

Various methods are disclosed for preparing quinoline-substituted intermediates from which a carbonate, preferably t-butyl carbonate or carbamate compound, is obtained. Processes described and claimed herein employ alcohols, esters, acetals, aldehydes, and carboxylic acids as suitable intermediate compounds. The intermediate compounds provide a suitable substrate from which a quinoline-substituted alkenol is obtained or the intermediate is directly hydrogenated to obtain carbonate or carbamate derivatives of the invention.

In one aspect, the invention relates to a process of preparing a compound of the formula:

$$R^1-CH=CHCH_2OC(O)-X-R^2 \quad (I),$$

wherein $R^1$ is independently selected from hydrogen and quinolyl optionally substituted with one or more of:
(i) alkyl,
(ii) alkoxy,
(iii) aryl,
(iv) nitro, and
(v) halo;

$R^2$ is $C_1-C_{10}$-alkyl; X is —O— or —$NR^3$; and $R^3$ is hydrogen, $C_1-C_6$-alkyl or aryl, or $R^2$ and $R^3$ taken together form an aromatic or non-aromatic ring. The process comprises the steps of:

(a) preparing an intermediate selected from the group consisting of:
(i) $R^1-C\equiv CCH_2OR^4$, wherein $R^4$ is hydrogen or a hydroxy protecting group;
(ii) $R^1-CH=CHC(O)OR^5$, wherein $R^5$ is $C_1$ to $C_6$ lower alkyl;
(iii) $R^1-CH=CHCH(OR^6)(OR^7)$, wherein $R^6$ and $R^7$ are independently $C_1$ to $C_6$ lower alkyl;
(iv) $R^1-CH=CHC(O)OH$;
(v) $R^1-CH=CHCHO$;
(vi) $R^1-C\equiv C-CH_2-OC(O)-X-R^2$; and (b) reducing or deprotecting an intermediate obtained in step (a); and (c) optionally coupling the compound obtained from step (b) with an acylating reagent.

Intermediates (i) through (v) can be reduced to provide the alkenol derivative. The alkenol undergoes a coupling reaction with an acylating reagent, for example acyl halides, acid anhydrides, carbamoyl halides, and acid derivatives of aromatic and non-aromatic heterocycles, to afford compounds of formula (I). Intermediate (vi) can be directly hydrogenated to provide compound (I).

Therefore, one process for preparing a compound of formula (I) via the alkenol generally comprises:

(a) preparing a compound of the formula $R^1-CH=CHCH_2OR^4$, wherein $R^1$ and $R^4$ are as previously defined;

(b) optionally deprotecting the compound obtained in step (a); and (c) reacting the compound of the formula $R^1-CH=CHCH_2OH$ with an acylating agent.

An alternative process for preparing the compound of formula (I) comprises:

(a) preparing a compound of the formula $R^1-C\equiv C-CH_2-OC(O)-X-R^2$, wherein $R^1$ and $R^2$ are as previously defined; and (b) hydrogenating the compound obtained in step (a).

In another aspect, the invention relates to a process of preparing a compound of the formula:

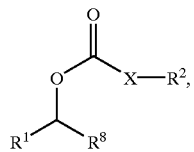

(II)

wherein
R$^1$, R$^2$ and X are as previously defined, and R$^8$ is selected from the group consisting of:
(i) —CH=CH—R$^{11}$; wherein R$^{11}$ is hydrogen or alkyl; and
(ii) —C≡CR$^{11}$.

The process comprises the steps of:
(a) reacting a compound of the formula:

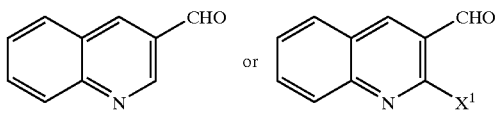

wherein X$^1$ is a halide, with an organometallic compound of the formula R$^8$—M or R$^8$—M—X$^1$, wherein R$^8$ and X$^1$ are as defined above and M is metal, and an acylating reagent;
(b) optionally hydrogenating the compound obtained in step (a), wherein R$^8$ is alkynyl or substituted alkynyl, to afford the corresponding compound wherein R$^8$ is alkenyl or substituted alkenyl.

Yet another aspect of the invention relates to preparing a compound of formula (I) or (II) as defined above.

In yet another aspect, the invention relates to the compounds selected from:
(a) R$^1$—CH=CHC(O)OR$^5$;
(b) R$^1$—CH=CHCH(OR$^6$)(OR$^7$);
(c) R$^1$—CH=CHC(O)OH;
(d) R$^1$—CH=CHCHO;
(e) R$^1$—C≡C—CH$_2$—OC(O)—X—R$^2$; and
(f) R$^1$—CH=CHCH$_2$OH;
wherein R$^1$, R$^2$, R$^5$, R$^6$ and R$^7$ are as previously defined.

Processes of the invention provide carbonate or carbamate compounds useful as intermediates in the synthesis of erythromycin derivatives, for example, macrolide antibiotics and erythromycin ketolide compounds. Compounds of formula (I) or (II) are suitable for preparing 6-O-substituted erythromycin derivatives having a 6-O-quinolyl-substituted propenyl substituent.

DETAILED DESCRIPTION OF THE INVENTION

A number of terms are used herein to designate particular elements of the present invention. When so used, the following meanings are intended:

The term "lower alkyl" or "alkyl" as used herein refers to straight or branched chain saturated hydrocarbon radicals. "C$_x$ to C$_y$ alkyl" and "C$_x$-C$_y$", wherein x and y are each an integer from 1 to 20, denotes an alkyl group containing the number of carbons as designated by x and y, for example, the term "C$_1$ to C$_6$ alkyl" refers to a straight or branched chain saturated hydrocarbon radical containing from 1 to 6 carbon atoms. Exemplary lower alkyl or alkyl groups include, but are not limited to, methyl, ethyl, n-propyl, isopropyl, n-butyl, isobutyl, sec-butyl, t-butyl, pentyl, hexyl, and the like.

The term "alkenyl" as used herein refers to straight- or branched-chain hydrocarbon radicals containing between two and six carbon atoms and possessing at least one carbon-carbon double bond. Examples of alkenyl radicals include vinyl, allyl, 2- or 3-butenyl, 2-, 3- or 4-pentenyl, 2-, 3-, 4-, or 5-hexenyl, and the like, and isomeric forms thereof.

The term "alkynyl" as used herein refers to straight or branched-chain hydrocarbon radicals containing between two and six carbon atoms and possessing at least one carbon-carbon triple bond. Examples of alkynyl radicals include ethynyl, propargyl, propylidyne, and the like, and isomeric forms thereof.

The term "polar aprotic solvent" refers to polar organic solvents lacking an easily removed proton including, but not limited to, N,N-dimethylformamide, N,N-dimethyl acetamide, N-methyl-2-pyrrolidone, hexamethylphosphoric triamide, tetrahydrofuran, 1,2-dimethoxyethane, acetonitrile, ethyl acetate, and the like, or a mixture thereof.

The term "acylating reagent" refers to a substituent capable of placing an acyl group or carbamoyl group onto a nucleophilic site including, but not limited to, acyl halides, acid anhydrides, carbamoyl halides, acid derivatives of aromatic and non-aromatic heterocycles, and the like. Exemplary acylating reagents include, but are not limited to, di-tert-butyl dicarbonate, di-isopropyl dicarbonate, t-butyl chloroformate (not commercially available), 2-(t-butoxycarbonyl-oxyimino)-2-phenylacetonitrile, N-t-butoxy-carbonyloxysuccinimide, 1-(t-butoxycarbonyl)-imidazole, dicyclohexylcarbamoyl chloride, diphenylcarbamoyl chloride, diisopropyl carbamoyl chloride, morpholine acid chloride, carbonyl diimidazole, and the like.

Commonly owned, U.S. Application Serial No. 60/140,968, filed on Jun. 24, 1999, describes a method for preparing 6-O-substituted macrolide derivatives which relates to the coupling of substituted or unsubstituted allyl carbonate or carbamate derivatives with a macrolide core, and particularly a ketolide core. The method exemplifies one method of a number of syntheses available introducing substituted or unsubstituted allyl carbonate and carbamate substituents onto a parent compound core.

Numerous processes for preparing the intermediates and the corresponding carbonate or carbamate compounds therefrom are described herein. Exemplary processes follow in Schemes 1–7, which are intended to illustrate a process of the invention and are not meant to limit the scope of the invention in any way. Isomeric forms of compounds described in the Schemes are contemplated and considered as encompassed within the scope of the claimed invention. Various changes and modifications to the disclosed embodiments will be apparent to those skilled in the art. Such changes and modifications are within the purview of the invention and can be made without departing from the spirit and scope thereof.

One manner of preparing the alkenol intermediate involves coupling a propargyl alcohol with a haloquinoline, and reducing the compound obtained therefrom to the corresponding alkenol as exemplified in Scheme 1, below.

Scheme 1

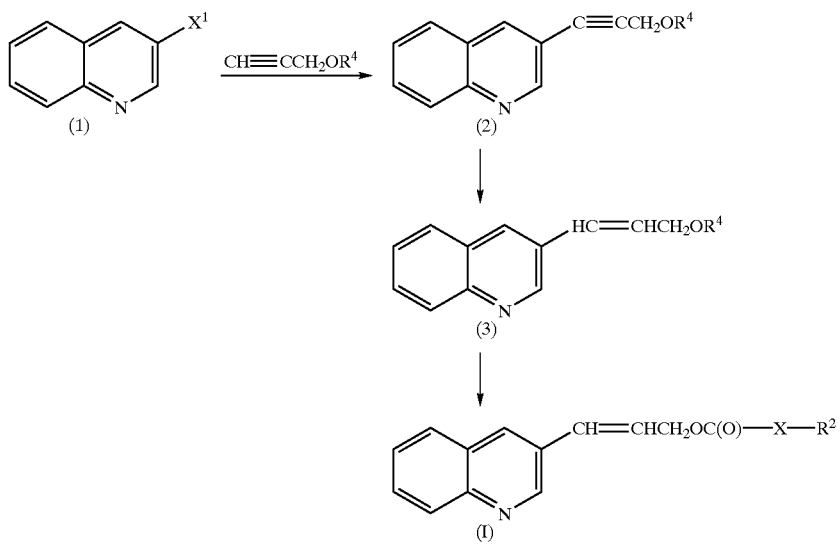

According to Scheme 1, a commercially available haloquinoline (1) wherein $X^1$ is bromine, chlorine, or iodine, is reacted with substituted or unsubstituted propargyl alcohol in the presence of a base and a palladium-based catalyst. The reaction is carried out at a temperature from 20° C. to 100° C. Preferably, the temperature is from about 25° C. to about 90° C.

The propargyl alcohol is either unsubstituted or substituted with a hydroxy protecting group $R^4$. The protecting group can be one of many commonly available hydroxy protecting groups. Typical hydroxy protecting groups for $R^4$ include, but are not limited to, tetrahydropyranyl, benzyl, trimethylsilyl, triisopropylsilyl, t-butyldimethylsilyl, t-butyldiphenylsilyl, formyl, acetyl, pivalyl, mesyl, and tosyl. A thorough discussion of protecting groups and the solvents in which they are most effective is provided by T. W. Greene and P. G. M. Wuts in *Protective Groups in Organic Synthesis*, 3rd ed., John Wiley & Son, Inc., 1999.

At least one carbon of the quinoline-based starting material is substituted with a halide selected from the group consisting of bromine, chlorine, and iodine, for example, bromoquinoline, chloroquinoline, and iodoquinoline. The haloquinoline is optionally substituted with aliphatic or aromatic substituents as well as nitrogen-containing moieties including, but not limited to, alkyl, alkoxy, aryl, and nitro.

The catalyst used is either the 0-valent palladium species or it is generated in-situ, such as palladiumtriphenyl phosphine, by the methods known in the art. See for example, Beller et al. *Angew. Chem. Int. Ed. Engl.*, 1995, 34(17), 1848. The palladium catalyst can be selected from the group consisting of palladium acetate, tetrakis (triphenylphosphine)-palladium, and tris (dibenzylideneacetate)dipalladium.

Treatment with palladium acetate or palladium on carbon proceeds in a facile manner when used with a promoter, preferably a phosphine. A suitable phosphine is selected from triphenylphosphine, bis(diphenylphosphine)methane, bis(diphenylphosphine)ethane, bis(diphenylphosphine) propane, 1,4-bis(diphenylphosphine)butane, bis (diphenylphosphine)-pentane, tri(o-tolyl)phosphine, and the like. The ratio of palladium catalyst to the phosphine generally ranges from 1:1 to about 1:8.

A halide, such as a copper halide or phase transfer catalyst, such as a tetrabutylammonium halide or tetrabutylammonium hydrogen sulfate, can be used with the palladium-based catalysts to enhance the coupling reation. The preferred copper halides are copper bromide and copper iodide. Preferably, the phase transfer catalyst is tetrabutylammonium bromide.

Useful bases for the invention are organic or inorganic bases. Exemplary inorganic bases include, but are not limited to, sodium hydroxide, potassium hydroxide, ammonium hydroxide, sodium carbonate, potassium carbonate, ammonium carbonate, and the like, or a mixture thereof.

Organic bases include, but are not limited to, dimethylaminopyridine, pyridine, dimethylamine, diethylamine, diisopropylamine, diisopropylethylamine, triethylamine, piperidine, pyrrolidine, pyrrole, triisopropylamine, and the like, or a mixture thereof.

The reaction can be carried out in an aprotic solvent. Typical aprotic solvents are selected from N,N-dimethylformamide, N,N-dimethyl acetamide, dimethyl sulfoxide, N-methyl-2-pyrrolidone, hexamethylphosphoric triamide, tetrahydrofuran, 1,2-dimethoxyethane, methyl-t-butyl ether, toluene, heptane, acetonitrile and ethyl acetate. The preferred solvent is acetonitrile and N,N-dimethylformamide.

Exemplary conditions in which the reaction is carried out are described below in Table 1.

TABLE 1

| Alcohol | Amine | Catalyst/Promoter | Temp. | Solvent |
| --- | --- | --- | --- | --- |
| Propargyl alcohol | Et$_3$N | Pd(PPh$_3$)$_2$Cl$_2$ | 90° C. | CuI, Et$_3$N |
| | (iPr)$_2$NH | Pd(PPh$_3$)$_2$Cl$_2$ | 75° C. | CuI, EtOAc |
| | piperidine, nBu$_4$NBr | Pd(OAc)$_2$, PPh$_3$ | 45° C. | CH$_3$CN, |
| | K$_2$CO$_3$, CuBr | 10% Pd/C, PPh$_3$ | 75° C. | CH$_3$CN, |
| | piperidine, nBu$_4$NBr | 5% Pd/C, PPh$_3$ | 50° C. | CH$_3$CN, |

Conditions described above in Table 1 are meant to be illustrative and are not intended to limit the scope of the invention in any way.

The alkynol (2) obtained from the coupling reaction can be reduced to provide an alkenol (3). The alkynol (2) can be reduced either by catalytic semi-hydrogenation or reduction with an aluminum hydride-type reagent, which respectively produce the cis and the trans isomers of an alkenol intermediate, as illustrated below.

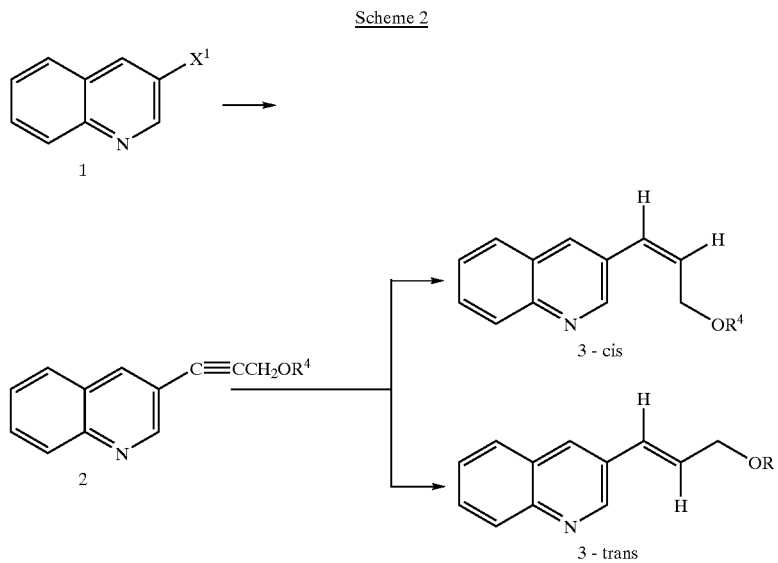

Scheme 2

In Scheme 2, the cis isomer (3-cis) of the alkenol can be prepared by catalytic semi-hydrogenation using hydrogen gas or by catalytic transfer hydrogenation using a hydrogen donor source, such as ammonium formate, formic acid, benzyltriethylammonium formate, hydrazine, cyclohexadiene, and the like, or a mixture thereof. Both methods employ a metal catalyst, such as palladium, platinum, or nickel. Typical catalysts for the semi-hydrogenation include, but are not limited to, bis-dichloro triphenylphosphine palladium(II), palladium acetate, tetrakis(triphenylphosphine)palladium, tris (dibenzylideneacetone)dipalladium, palladium on carbon, palladium on calcium carbonate, palladium on barium sulfate, Raney Nickel, and platinum black oxide.

Certain additives are suitable for the catalytic semi-hydrogenation and can afford the cis isomer with improved yields. One suitable additive is 3,6-dithia-1,8-octanediol, however, various other additives can be used in the hydrogenation.

Reacting the alkynol with an aluminum hydride type reagents affords the trans isomer (3-trans). Typically, the reaction is carried out from −20° C. to 25° C. Aluminum hydride type reagent suitable for the reaction are, for example, lithium aluminum hydride, diisobutylaluminum hydride, or Red-Al (sodium bis(2-methoxyethoxy) aluminum hydride in toluene). About 1 to about 2 molar equivalents of the aluminum hydride are reacted with one equivalent of the 3-(3-quinolyl)-2-propyn-1-ol starting material.

Suitable reaction medium for the aluminum hydride-type reduction is anhydrous tetrahydrofuran. The reaction can also be carried out in polar aprotic solvents, such as dimethoxyethane or methyl-t-butyl ether, and nonpolar aprotic solvents, such as toluene.

When $R^4$ of the alkenol is a hydroxy protecting group, the compound is deprotected prior to converting the alcohol to a carbonate or carbamate moiety. Deprotection of the hydroxy group can be accomplished under acidic or basic conditions depending on the nature of the protecting group by standard methods known in the art. A summary of the procedures suitable for deprotecting the hydroxy group is described in T. W. Greene and P. G. M. Wuts in *Protective Groups in Organic Synthesis*, $2^{nd}$ ed., John Wiley & Son, Inc., 1991, which is herein incorporated by reference.

Conversion of alkenol (3) to the carbonate or carbamate derivatives can be carried out with a wide variety of reagents. The product mixture obtained maintains the approximate proportions of cis to trans isomers which indicates the conversion preserves the orientation at the regiocenter as shown below.

also suitable for the reaction. Conversion of the alkenol proceeds in a more facile manner when from about 0.01 to about 0.05 molar equivalents of a phase transfer reagent relative to the alkenol starting material is added to the reaction mixture. A wide variety of phase transfer reagents are suitable for the reaction including, but not limited to, Scheme 3

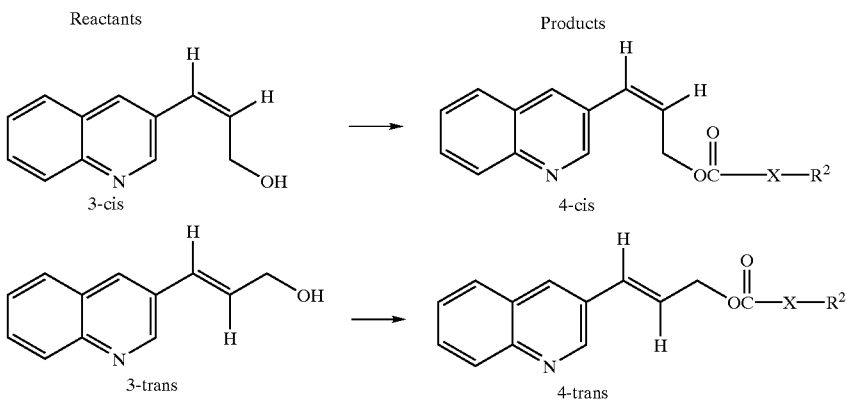

According to Scheme 3, an acylating reagent is reacted with a quinoline-substituted alkenol (3-cis or 3-trans) obtained from the reduction reaction to convert the alcohol to a desired carbonate or carbamate derivative of formula (I), the cis and trans isomers of which correspond to compounds (4-cis) and (4-trans), wherein X is —O— and $R^2$ is $C_1$–$C_{10}$-alkyl, respectively. The reaction is carried out in an aprotic solvent at temperatures from about –30° C. to 50° C. Introducing either an organic or an inorganic base facilitates the reaction.

The acylating reagent places group of the formula

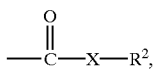

wherein X and $R^2$ are as previously defined, onto the oxygen atom of the hydroxy moiety. Acylating reagents suitable for preparing the carbonate derivatives are typically acyl halides and acid anhydrides, which include, but are not limited to, di-tert-butyl dicarbonate and di-isopropyl dicarbonate. Other exemplary reagents include are t-butyl chloroformate, 2-(t-butoxy-carbonyloxyimino)-2-phenylacetonitrile, N-t-butoxycarbonyloxy-succinimide, and 1-(t-butoxy-carbonyl) imidazole, and the like. For preparing the preferred carbonate, 3-(3-quinolyl)-2-propen-1-ol t-butyl carbonate the 3-(3-quinolyl)-2-propen-1-ol intermediate is preferably treated with di-tert-butyl dicarbonate.

Carbamate derivatives of formula (I) can be prepared by reacting the alkenol, with a suitable carbamoyl chloride or the acid chloride of an aromatic or non-aromatic nitrogen heterocycle in the presence of base. Exemplary acylating reagents for preparing the carbamate compounds are selected from carbamoyl halides and acid derivatives of aromatic and non-aromatic nitrogen containing heterocycles, including but not limited to, dicyclohexylcarbamoyl chloride, diphenylcarbamoyl chloride, diisopropyl carbamoyl chloride, morpholine acid chloride, carbonyl diimidazole, and the like.

Aprotic solvents are selected from the group as described above. The preferred solvent is toluene. Dichloromethane is n-tetrabutylammonium halides and n-tetrabutylammonium hydrogen sulfate. The preferred phase transfer reagent is n-tetrabutylammonium hydrogen sulfate.

Alternatively, the alkynol (2) is coupled with the acylating reagent to afford a carbonate or carbamate intermediate of the formula $R^1$—C≡C—$CH_2$—OC(O)—X—$R^2$, wherein $R^1$ and $R^2$ are previously defined, which can be reduced to provide the alkenyl carbonate or carbamate compounds of formula (I). The intermediate can be reduced by way of catalytic semi-hydrogenation to provide the derivative of formula (I). Preferably, the intermediate is reduced using 5% palladium on calcium carbonate poisoned with lead (Lindlar's catalyst, $Pd/CaCO_3/Pb$) and hydrogen gas, which provides the cis isomer (3-cis). The portion of Lindlar's catalyst reacted with one equivalent of the alkynol starting material is from about 0.005 to about 0.2 weight/weight equivalents.

One alternate method of preparing the carbonate relates to treating a haloquinoline with propargyl alcohol, a copper halide, or more preferably copper iodide, and dichlorobis-(triphenylphosphine)palladium(II) in the presence of triethylamine in an aprotic solvent. The alkynol obtained therefrom is reduced by methods of hydrogenation or Red-Al reduction to afford an alkenol, which can be coupled with an acylating agent to provide a desired derivative.

Another preferred method of preparing the alkynol involves reacting a haloquinoline with propargyl alcohol, tetrabutylammonium bromide, and palladium acetate or palladium on carbon in combination with a phosphine. The reaction is accomplished in the presence of a secondary amine, such as piperidine, or acetonitrile or mixtures of THF and water. Reduction of the alkynol with Red-Al is accomplished with tetrahydrofuran solvent and the resulting alkenol is coupled with an acylating reagent, such as di-tert-butyl dicarbonate, in the presence of base and tetrabutylammonium hydrogen sulfate in dichloromethane or toluene.

Preferably, the haloquinoline starting material is selected from 3-bromoquinoline or 3-iodoquinoline. The most preferred haloquinoline is 3-bromoquinoline.

Other possible methods for preparing the alkenol involve using acrolein acetal or vinyl ester reagents as described in the following Scheme.

Scheme 4

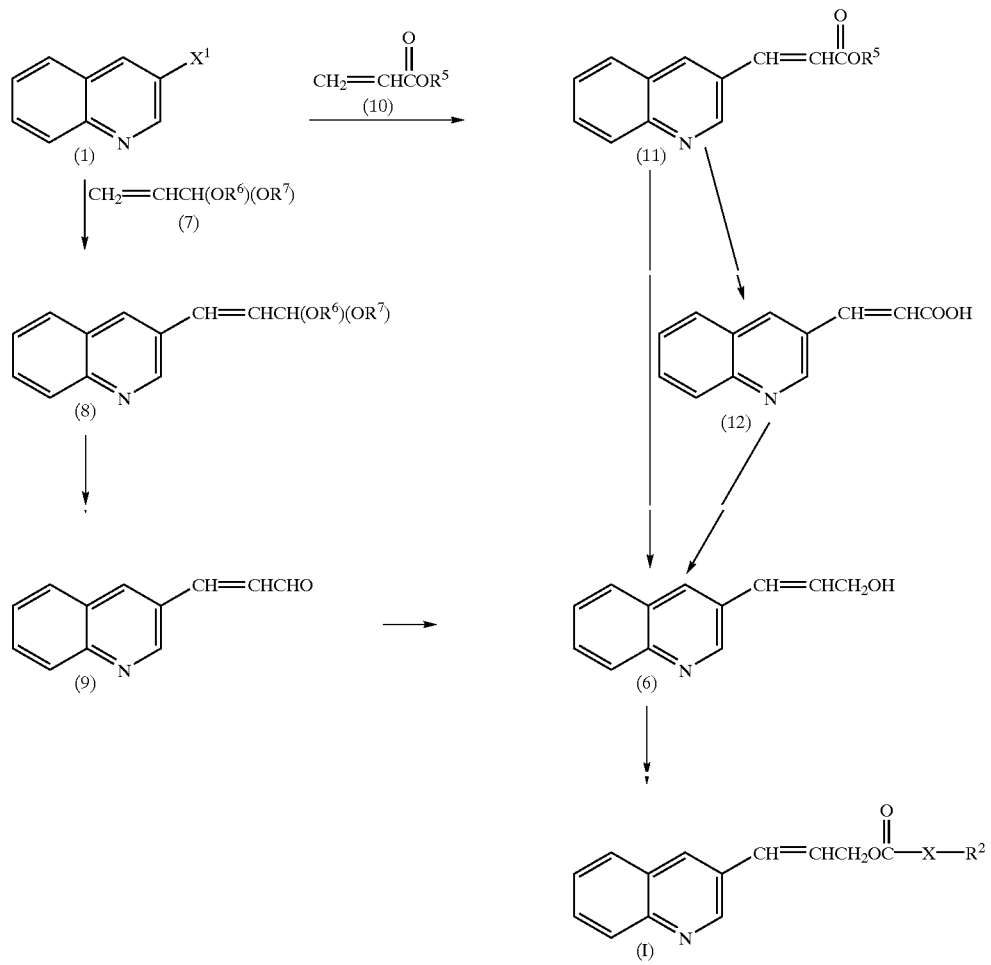

As illustrated in Scheme 4, a haloquinoline couples (1) with an acrolein acetal (7) having a formula $CH_2=CHCH(OR^6)(OR^7)$, wherein $R^6$ and $R^7$ are independently $C_1$ to $C_6$ alkyl, via a palladium-catalyzed reaction in the presence of a base. The reaction is carried out at a temperature from about 90° C. to about 110° C. in a polar aprotic solvent.

Palladium catalysts suitable for coupling the propargyl alcohol with the haloquinoline can also be used for the reacting the starting material with the acrolein acetal. Acrolein acetals suitable for the coupling include, but are not limited to, acrolein dimethylacetal, acrolein diethylacetal, acrolein diisopropylacetal, acrolein n-dibutylacetal, acrolein n-dipentylacetal, acrolein ethylmethylacetal, acrolein isopropylmethylacetal, and the like. Portions of the acrolein acetal used relative to the haloquinoline generally ranges from about 1:1 to about 4:1

A phosphine is optionally used with the palladium acetate catalyst. Suitable phosphines are selected from the group as described above relating to the coupling of the alkynol in Scheme 1. Preferably, the phosphine for coupling the acrolein acetal with the haloquinoline is tri(o-tolyl) phosphine. Portions of the phosphine relative to portions of the palladium catalyst generally range from about 1:1 to about 8:1.

Addition of a phase transfer agent, preferably tetrabutylammonium hydrogen sulfate, provides the carbonate.

An inorganic or organic base is suitable for the reaction, and selected from the group described above. The reaction is carried out in an aprotic solvent as previously described.

The carboxaldehyde acetal (8) wherein $R^6$ and $R^7$ are independently $C_1$ to $C_6$ alkyl, obtained therefrom is then treated with an acid to produce the acrolein (9). The acid is selected from a wide variety of inorganic and organic acids selected from hydrochloric acid, sulfuric acid, formic acid, acetic acid, propionic acid, butyric acid, tartaric acid, citric acid, trifluoroacetic acid, p-toluensulfonic acid, pyridinium p-toluenesulfonic acid, and the like, or a mixture thereof.

The preparation of the acrolein allows for using milder reducing agents, such as borane complex reagents, during reduction. Reduction of the acrolein with a borane complex reagent provides the alkenol, which can be converted into the carbonate or carbamate derivatives of formula (I) as previously described. The reduction is accomplished at room temperature in an aprotic solvent selected from the group described above for the coupling the alkynol to the haloquinoline. Exemplary borane complex reagents include, but are not limited to, borane-dimethyl sulfide, borane-tetrahydrofuran complex, borane-pyridine complex, borane-morpholine, borane-trimethylamine complex, borane t-butylamine, borane-N,N-diisopropylethylamine, borane dimethylamine, 4-(borane-dimethylamino)pyridine, borane- 4-ethylmorpholine, and borane-4-methylmorpholine. From about 0.25 to about 1 equivalent of borane complex is reacted with 1 equivalent of the 3-(3-quinolyl)acrolein. The most preferred borane complex reagent is borane t-butylamine.

Similarly, borohydride reducing reagents are suitable for the reaction. Typical borohydride reducing reagents are selected from borane, borane-methyl sulfide, borane-methylsulfide with additives such as $BF_3 \cdot OEt_2$ or $B(OMe)_3$, 9-borabicyclononane, lithium borohydride, sodium borohydride alone or with additives such as $AlCl_3$ or $TiCl_4$, lithium borohydride, and potassium borohydride.

Aluminum hydride reducing reagents, for example diisobutyl aluminum hydride and lithium aluminium hydride alone or with $AlCl_3$, are also suitable for the reduction.

The palladium coupling reaction can also be carried out using a vinyl ester (10) of the formula $CH_2=CHC(O)OR^5$, wherein $R^5$ is $C_1$ to $C_6$ alkyl, for preparing 3-(quinolyl-substituted)-2-propen-1-alkyl ester (11), wherein $R^5$ is $C_1$ to $C_6$ alkyl. Treating a haloquinoline with a vinyl ester and palladium acetate yields the alkyl ester absent the use of a phosphine. The reaction is carried out in an aprotic solvent in the presence of base with the addition of a phase transfer reagent, such as tetrabutylammonium bromide or tetrabutylammonium chloride.

Exemplary vinyl esters suitable for the reaction include, but are not limited to, methyl acrylate, ethyl acrylate, and the like.

The alkenol starting material for the conversion reaction is obtained from the alkyl ester in one of two ways. Direct reduction of the alkyl ester with an aluminum hydride reagent as detailed above in Scheme 1 provides the alcohol under conditions as previously described. Treating the alkyl ester (11) at ambient temperature with from about 1 to about 10 molar equivalents of base for each equivalent of the alkyl ester affords carboxylic acid (12), which can be further reduced to the alcohol under mild reduction conditions with a boron reducing reagent, such as borohydrides or borane complex reducing agents.

Various processes yield secondary carbonate derivatives, which are described in accordance with another aspect of the invention. The compounds of the formula:

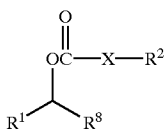

wherein $R^1$ is independently selected from hydrogen and quinolyl optionally substituted with one or more of (i) alkyl, (ii) alkoxy, (iii) aryl, (iv) nitro, and (v) halo; $R^2$ is $C_1-C_{10}$-alkyl; X is —O— or —$NR^3$, wherein $R^3$ is hydrogen, $C_1-C_6$-alkyl or aryl, or $R^2$ and $R^3$ taken together form an aromatic or non-aromatic ring; and $R^8$ is —CH=CH—$R^{11}$ or —C≡$CR^{11}$, wherein $R^{11}$ is hydrogen or alkyl; can be used as intermediates in the 6-O-alkylation of macrolide antibiotic and ketolide compounds. Alkylation of the 6-O-position of an erythromycin derivative is accomplished in a manner similar to the synthesis using the primary carbonate, as described in the U.S. Application Ser. No. 60/140,968.

The secondary carbonate or carbamate derivatives can be prepared by one of at least two syntheses. In one method, a 2-halo-quinoline-3-carboxaldehyde starting material is treated with an organometallic reagent and an acylating agent to obtain a compound of the desired formula. In another method, a quinoline carboxaldehyde is reacted with an organometallic reagent followed by treatment with an organolithium compound. The compound is reacted with acylating reagent to provide compounds of formula (III), as illustrated below.

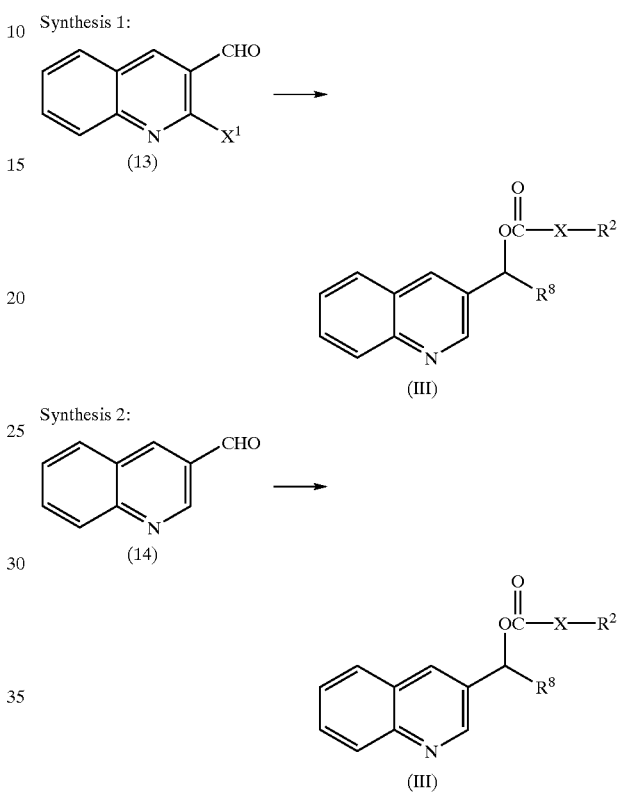

A 2-halo-3-quinoline carboxaldehyde (13) can be reacted with an organometallic reagent $R^8$—M or $R^8$—M—$X^1$, wherein $R^8$ is as defined above, M represents a metal, and $X^1$ is a halide, and treated with an acylating reagent to provide a protected secondary carbonate. Preferably, the haloquinoline carboxaldehyde is 2-iodo-3-quinoline carboxaldehyde. Reaction with the organometallic reagent is accomplished in an aprotic solvent. Exemplary organometallic reagents are vinyl magnesium bromide, vinyl magnesium chloride, and the like. A suitable lithium reagent can be reacted with the product obtained therefrom and followed by a suitable acylating reagent to provide the secondary carbonate.

Suitable organolithium reagents are alkyl lithium reagents. The preferred alkyl lithium reagent is n-butyllithium.

Reaction of an organometallic reagent with a quinoline carboxaldehyde (14) and an acylating reagent affords compounds of formula (III). The preferred reagent, quinoline-3-carboxaldehyde, is a commercially available compound. However, the cost for the material is expensive ($230/5 g, Aldrich, Milwaukee, Wis., U.S.A.). Novel processes for preparing the starting material provide a more efficient and cost effective synthesis and can be used for the preparation of a quinoline carboxaldehyde material or in accordance with a process for preparing quinoline-substituted carbonate, as illustrated below.

Scheme 6

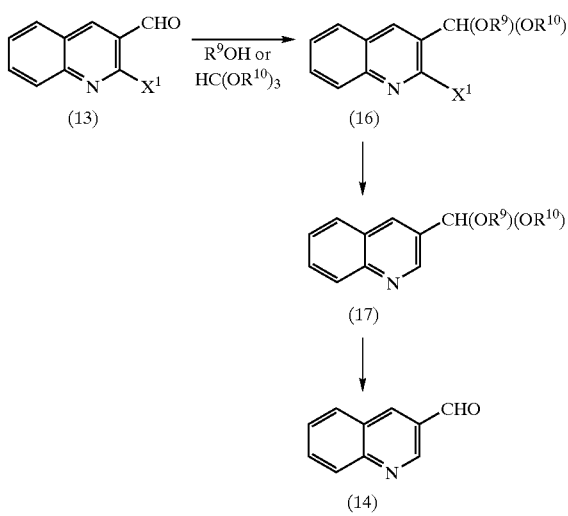

The starting material for the carboxaldehyde synthesis (13), wherein $X^1$ is a halide, can be prepared by Vilsmeier-Haack formylation of an acetanilide as described by Meth-Cohn, et al. in *J. C. S. Perkin I*, 1520–1530 (1981). The quinoline-2-halo-3-carboxaldehyde is isolated and dried to obtain the starting material or, alternatively, an alcohol or orthoformate reagent is directly charged into the reaction mixture to obtain the quinoline-2-halo-3-carboxaldehyde acetal (16), wherein $R^9$ and $R^{10}$ are independently $C_1$ to $C_6$ alkyl.

Reagents useful for the reaction are alcohols represented by the formula $R^9$—OH or orthoformates represented by the formula $HC(OR^{10})_3$, wherein $R^9$ is $C_1$ to $C_6$ alkyl and $R^{10}$ is $C_1$ to $C_3$ alkyl. An alcohol suitable for the invention is selected from methanol, ethanol, isopropanol, butanol, pentanol, and hexanol, or a mixture thereof. Examples of useful orthoesters are trimethyl orthoformate, triethyl orthoformate, triisopropyl orthoformate, and the like. Trace amounts of organic or inorganic acid facilitate the conversion, such as those typically selected from acetic acid, formic acid, p-toluenesulfonic acid, hydrochloric acid, phosphoric acid, sulfuric acid, and the like.

Removing the halo group of the quinoline-2-halo-3-carboxaldehyde acetal is accomplished by treatment with a metal catalyst and hydrogen in the presence of a base. The metal catalysts include, but are not limited to, palladium, organopalladium, and platinum-based compounds. Examples of suitable metal catalysts are palladium black oxide, palladium on charcoal, palladium acetate, palladium chloride, triarylphosphine palladium complexes, platinum black oxide, and the like. A summary of suitable reagents and conditions for metal-catalyzed coupling reactions are described in Heck et al., *J. Org. Chem.*, 1972 37, 2320.

The reaction is carried out in an organic solvent in the presence of from about 1 to about 6 molar equivalents of base relative to the carboxaldehyde acetal starting material. Preferably, about 4 molar equivalents of base is used. Exemplary solvents used are organic solvents, such as acetonitrile, N,N-dimethylformamide, N-methylpyrrolidinone, methanol, ethanol, isopropanol, and the like, or a mixture thereof. Organic base, for example amines, and inorganic bases are suitable for the reaction. Amines that are useful include, but are not limited to, secondary and tertiary amines, such as dimethylamine, diethylamine, triethylamine, diisopropylethylamine, diethylaminopyridine, and pyridine. Inorganic bases are selected from sodium hydroxide, potassium hydroxide, ammonium hydroxide, sodium carbonate, potassium carbonate, ammonium carbonate, and the like.

The carboxaldehyde (14) is obtained from carboxaldehyde acetal (17) by hydrolysis with an acid carried out in organic or inorganic solvent. The acids are organic and inorganic acids. Suitable inorganic acids include sulfuric acid, hydrochloric acid, and the like. The preferred solvents are organic solvents, such as methanol, ethanol, isopropanol, and the like. Preferably, the weak acids are formic acid and acetic acid.

The carboxaldehyde provides a suitable starting material for the synthesis of the primary and secondary carbonate derivatives. The addition of an organometallic reagent compound to the carboxaldehyde generates an intermediate complex, which is coupled to an acylating reagent, for example di-tert-butyl dicarbonate and di-isopropyl dicarbonate, to prepare a carbonate. Other exemplary acylating reagents are as described above. Carbamate derivatives of the invention can be prepared by using carbamoyl chlorides or acid chlorides of aromatic or non-aromatic nitrogen heterocycles.

Suitable organometallic reagents are represented by the formula $R^8$—M and $R^8$—M—$X^1$, wherein $R^8$ is substituted or unsubstituted $C_1$–$C_6$ alkenyl or $C_1$–$C_6$ alkynyl, such as substituents of the formula —CH=CH—$R^{11}$ and —C≡C—$R^{11}$, wherein $R^{11}$ is hydrogen or alkyl, M represents a metal, and $X^1$ is a halide. Preferably, the organometallic reagent used is an organolithium or an organomagnesium reagent, such as a Grignard reagent. The preferred reagents are selected from reagents of the formulas $R^8$—M and $R^8$—M—$X^1$, wherein M is lithium or magnesium and X is bromine, chlorine, and iodine. Common Grignard reagents as described in accordance with the Y. H. Lai, *Synthesis* 1981, 104, which is herein incorporated by reference. Exemplary organometallic reagents are t-butyl lithium, diethylmagnesium, ethynylmagnesium bromide, ethynylmagnesium chloride, vinylmagnesium bromide, vinylmagnesium chloride, and the like.

The reaction is accomplished in an aprotic solvent selected from the group described above for the preparation of the alkynol. Suitable temperatures for the reaction are from about −10° C. to about −15° C.

Alkyne-1-substituted quinoline compounds of formula (II), wherein $R^8$ is —C≡C—$R^{11}$ can be optionally reduced to the corresponding alkenyl-substituted carbonate by a palladium-catalyzed hydrogenation reaction using hydrogen gas. The preferred palladium catalyst for reducing the alkyne-1-substituted quinoline carbonate is Lindlar's catalyst (5% palladium on calcium carbonate poisoned with lead or Pd/$CaCO_3$/Pb).

The reaction is carried out in a polar organic solvent selected from the group consisting of tetrahydrofuran, N,N-dimethylformamide, and isopropanol.

The carboxaldehyde (14) can also undergo condensation with an acetate ester (18), wherein $R^5$ is $C_1$ to $C_6$ alkyl, with either an organic or inorganic base to provide a primary carbonate or carbamate, which is describe in accordance with the Scheme 7 below.

Scheme 7

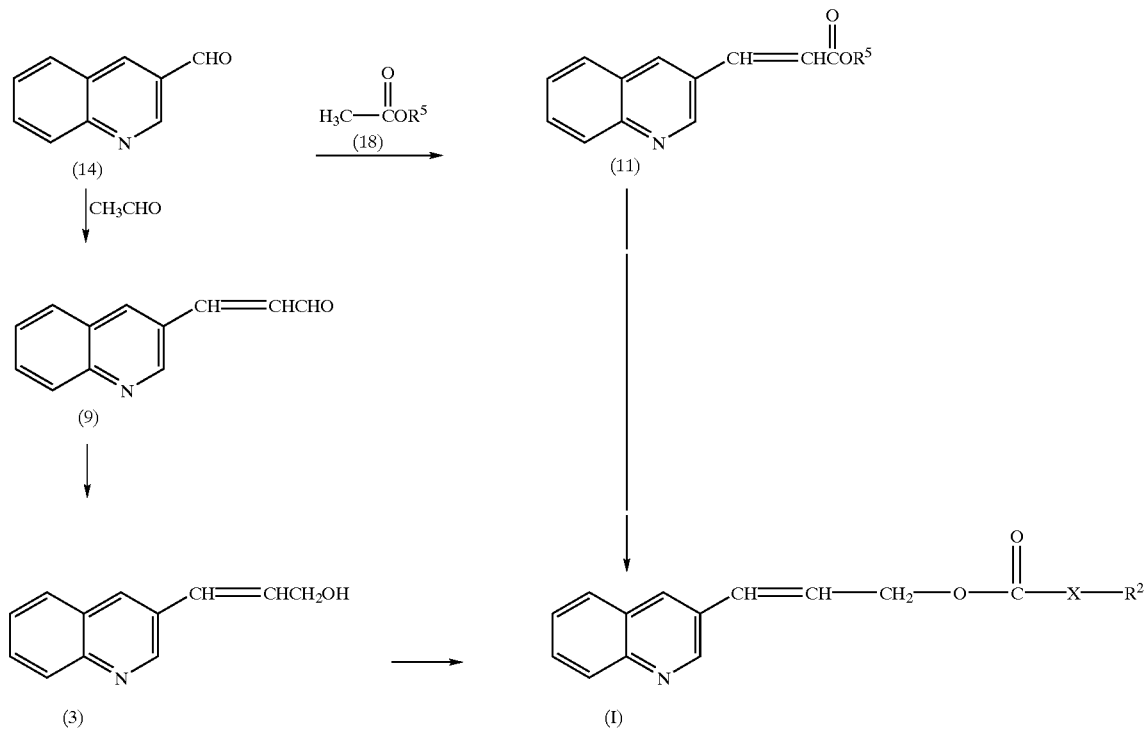

A suitable acetate ester for the reaction is represented by the formula $H_3C—C(O)(OR^5)$, (18) wherein $R^5$ is $C_1$ to $C_6$ alkyl, selected from methyl, ethyl, n-propyl, isopropyl, n-butyl, sec-butyl, t-butyl, and the like. Preferably, about 0.5 molar equivalents to about 2 molar equivalents of base are used relative to the carboxaldehyde. Typical bases for the reaction include, but are not limited to, potassium t-butoxide, sodium t-butoxide, sodium hydride, potassium carbonate, sodium ethoxide, sodium methoxide, 1,8-diazabicyclo[5.4.0]undec-7-ene, sodium hexamethyldisilazane, lithium hexamethyldisilazane, lithium diisopropylamide, and the like. Potassium t-butoxide is the preferred base.

Condensation of acetaldehyde with the carboxaldehyde (14) affords the acrolein intermediate (9) using relatively inexpensive reagents. The condensation can be carried out with acetic anhydride in the presence of an acid. Reduction of the product obtained therefrom provides the corresponding alkenol. The preferred method for reducing the acrolein intermediate is reduction with a borohydride reagent, such as sodium borohydride.

The processes described for the invention are particularly useful for preparing 3-(3-quinolyl)-2-propenyl derivatives, which are compounds of formula (I) and have the preferred structure for the 6-O-allylation reaction of macrolide antibiotics. To obtain 3-(3-quinolyl)-2-propen-1-ol t-butyl carbonate, for example, 3-bromoquinoline is coupled with propargyl alcohol, and reduced by methods of catalytic semi-hydrogenation to obtain 3-(3-quinolyl)-2-propen-1-ol. The 3-(3-quinolyl)-2-propen-1-ol is coupled with an acylating reagent capable of placing a t-butyl group on the oxygen atom of the terminal hydroxy group, preferably di-tert-butyl dicarbonate, to afford 3-(3-quinolyl)-2-propen-1-ol t-butyl carbonate.

In another preferred process, the 3-(3-quinolyl)-2-propyn-1-ol is coupled with an acylating reagent to provide a carbonate or carbamate derivatives, which can be hydrogenated to provide a compound of formula (I). The preferred acylating reagent for the reaction is di-tert-butyl dicarbonate.

In yet another preferred process, the 2-chloro-3-quinoline carboxaldehyde is converted into 2-iodo-3-quinoline and reacted with vinyl magnesium bromide followed by n-butyllithium and an acylating agent, preferably di-tert-butyl dicarbonate. The 1-(3-quinolyl)-2-propen-1-ol t-butyl carbonate prepared by the process is a compound of formula (II).

The processes for preparing a compound of formula (I) via the alkenol intermediate can be generally described as comprising the steps of:

(a) preparing a compound of the formula $R^1$—CH=CHCH$_2$OR$^4$, wherein $R^1$ and $R^4$ are as previously defined;

(b) optionally deprotecting the compound obtained in step (a); and (c) reacting the compound of the formula $R^1$—CH=CHCH$_2$OH with an acylating agent.

An alternative process for preparing the compounds of formula (I) comprises:

(a) preparing a compound of the formula $R^1$—C≡C—CH$_2$—OC(O)—X—R$^2$, wherein $R^1$ and $R^2$ are as previously defined; and (b) hydrogenating the compound obtained in step (a).

The alternative process allows for preparation of the carbonate and carbamate derivatives by directly coupling a propargyl alcohol derivative with an acylating reagent and hydrogenating the alkyne bond to obtain a desired compound.

In another aspect, the invention relates to a compound having the formula

or

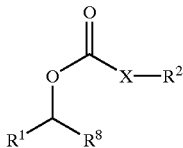

wherein

X is —O— or —NR$^3$—;

R$^1$ is independently selected from hydrogen and quinolyl optionally substituted with one or more substituents selected from:
(i) alkyl,
(ii) alkoxy,
(iii) aryl,
(iv) nitro, and
(v) halo;

R$^2$ is C$_1$–C$_{10}$-alkyl;

R$^3$ is hydrogen or C$_1$–C$_6$-alkyl; or R$^2$ and R$^3$ taken together form an aromatic or non-aromatic ring; and R$^8$ is selected from:
(i) —CH=CH—R$^{11}$; and
(ii) —C≡CR$^{11}$, wherein R$^{11}$ is hydrogen or alkyl.

The invention also relates intermediate compounds having the formula:

(a) R$^1$—CH=CHC(O)OR$^5$, wherein R$^1$ is independently selected from hydrogen and quinolyl optionally substituted with one or substituent selected from (i) alkyl, (ii) alkoxy, (iii) aryl, (iv) nitro, and (v) halo; and R$^5$ is C$_1$ to C$_6$ lower alkyl;

(b) R$^1$—CH=CHCH(OR$^6$)(OR$^7$), wherein R$^6$ and R$^7$ are independently C$_1$ to C$_6$ alkyl;

(c) R$^1$—CH=CHC(O)OH;

(d) R$^1$—CH=CHCHO;

(e) R$^1$—C≡C—CH$_2$—OC(O)—X—R$^2$; wherein R$^2$ is C$_1$–C$_{10}$-alkyl; X is —O— or —NR$^3$; and R$^3$ is hydrogen, C$_1$–C$_6$-alkyl or aryl; or R$^2$ and R$^3$ taken together form an aromatic or non-aromatic ring; or (f) R$^1$—CH=CHCH$_2$OH.

The intermediates are prepared by processes previously described and provide useful compounds in obtaining the desired carbonates and carbamates of formulas (I), (II) and (III).

Processes of the invention are better understood by reference to the following Reference Example and Examples. Various changes and modification may be made by one having ordinary skill in the art without departing from the scope of the invention. The Reference Example and the Examples are intended to provide illustration for a better understanding of the invention and are not meant to limit the invention in any way.

EXAMPLES

Reference Example 1

The following Reference Example illustrates a method for preparing the quinoline-2-chloro-3-carboxaldehyde compound, which can be used as a starting material for the preparation of quinoline-3-carboxaldehyde.

Reference Example 1:

Quinoline-2-chloro-3-carboxaldehyde

To 1-L three-necked flask equipped with mechanical stirrer, temperature probe, pressure equalizing dropping addition funnel, and dry nitrogen line was charged with dimethyl formamide (54.1 g, 0.74 mol). The contents were cooled to 0–5° C. in an ice/salt/water bath. Phosphorous oxychloride (317.5 g, 2.07 moles) was slowly charged into the mixture while monitoring the internal temperature of NMT +10° C. The addition typically required 30 minutes. The resultant slurry was mixed at 0–5° C. for 30 minutes. Acetanilide (40.0 g, 0.296 mol) was charged in a single portion via the pressure equalizing dropping addition funnel. The cooling bath was removed and the reaction mixture was warmed to 75° C. The reaction was monitored by thin layer chromatography (40:60 ethyl acetate/heptane). After completion of the reaction, the mixture was cooled to room temperature and then transferred to a dropping addition funnel. The mixture was added dropwise to 1.5 liter of water cooled to 0–5° C. contained in a 3-L three-necked flask equipped with mechanical stirrer and cooled in an ice/saltwater bath. The resultant yellow slurry was stirred at 0–5° C. for 30 minutes, and then filtered. The solid was filtered and washed with water to neutrality, then air dried. The solid was then dried in a vacuum oven at 40° C. over a period of 2 days to yield 39.0 g of product as a light yellow, powdery solid.

Examples 1–8

Examples 1–8 illustrate methods for preparing 3-(3-quinolyl)-2-propen-1-ol t-butyl carbonate of formula (1).

Example 1

Preparation of 3-(3-Quinolyl)-2-Propen-1-ol t-Butyl Carbonate

Step (1)

Preparation of 3-(3-quinolyl)-2-propyn-1-ol (Scheme 1, Compound (2))

To a dry 2-L three-necked flask previously purged with nitrogen was charged 3-bromoquinoline (118.77 g, 570 mmol), propargyl alcohol (71.9 g, 1.28 mol, 2.25 equiv), triethylamine (1500 mL), copper(I) iodide (3.62, 19 mmol, 0.033 equiv) and dichlorobis(triphenyl-phosphine) palladium(II) (6.67 g, 9.5 mmol). The mixture which resulted was mechanically stirred and heated to reflux for 3 hours. Upon cooling the triethylamine solution was mechanically stirred and heated to reflux for 3 hours. Upon cooling, the triethylamine solution was filtered and washed with triethylamine (300 mL). The filtrate was then concentrated under reduced pressure to provide solids which were suspended in 5% aq. NaHCO$_3$ (600 mL) and extracted with ethyl acetate (1×600 mL). The solids which were left after filtration were treated in the same manner. The combined ethyl acetate extracts were stirred with silica gel (15 g) and decolorizing carbon (3 g) before being filtered through a bed of celite. The filtrate was concentrated under reduced pressure to provide a tan colored solid which was vacuum oven dried at 45° C. overnight. The 3-(3-quinolyl)-2-propyn-1-ol was isolated in 92.14 g (88.3% yield). MS(CI): (M+H)$^+$ at 184; $^1$H NMR (300 MHz CDCl$_3$) δ4.56 (s, 2H), 4.70 (s, broad, 1H), 7.57 (m, 1H), 7.70 (m, 1H), 7.77 (d, 1H), 8.10 (d, 1H), 8.10 (s, 1H), 9.05 (s, 1H).

Step (2A)

Preparation of cis 3-(3-quinolyl)-2-propen-1-ol (Scheme 2, Compound (3-cis))

To a 1-L three-necked round-bottom flask was charged 3-(3-quinolyl)-2-propyn-1-ol (31.65 g, 173 mmol), ethanol (550 mL) and 5% palladium on calcium carbonate poisoned with lead (Lindlar's catalyst, 750 mg, 0.024 equiv). The atmosphere above the heterogeneous mixture was purged with hydrogen after which time hydrogen was delivered to the reaction via a balloon. The progress of the reaction was monitored by TLC (1:1 ethyl acetate/heptane). Upon reaction completion (~16 hours), the mixture was purged with nitrogen and vacuum filtered through a bed of celite. The product filtrate was then concentrated under reduced pressure. The residue which resulted was dissolved in ethyl acetate (750 mL) and extracted with 2 N HCl (2×750 mL). The aqueous acidic product solution was then adjusted to pH 9 with 2 N NaOH and then back extracted with isopropyl acetate (2×700 mL). The organic was then dried over Na$_2$SO$_4$, filtered and concentrated to an oil under reduced pressure. The product oil 3-(3-quinolyl)-2-propene-1-ol (29.5 g, 92.2%), which consisted of a mixture of both cis- and trans-alkenols, was subjected to flash chromatography (1:1 ethyl acetate/heptane) to isolate pure cis-alkenol. Both the cis- and trans-alkenols were isolated and submitted for $^1$H NMR analysis. The coupling constant $J^{ab}$ for the cis-alkenol was found to be 11.67 Hz while $J^{ab}$ for the trans-alkenol was found to be 15.93 Hz.

Step (2B)

Preparation of trans 3-(3-quinolyl)-2-propen-1-ol (Scheme 2, Compound (3-trans))

To a dry, jacketed 250-mL three-necked round-bottom flask was charged sodium bis(2-methoxyethoxy)aluminum hydride (Red-Al, 70% wt. solution in toluene, 11.0 g, 38.1 mmol, 1.39 eq) and anhydrous THF (20 mL). To this precooled (0–2° C.) and magnetically stirred solution was added a THF (50 mL) solution of the 3-(3-quinolyl)-2-propyn-1-ol (5.0 g, 27.32 mmol) via pressure equalizing dropping funnel. The temperature was not allowed to rise above 15° C. After the addition was complete (20 minutes) the mixture was allowed to warm up to room temperature and stirred for one hour. The solution was then cooled to 0° C. and quenched by the addition of aqueous 10% sulfuric acid (20 mL) such that the internal temperature did not rise above 15° C. The biphasic reaction mixture was then washed with ethyl acetate (3×100 mL). The pH of the aqueous acidic product solution was then adjusted to pH 9–10 with aq. conc. NH$_4$OH and back extracted into ethyl acetate (2×125 mL). The combined organic layers were dried over anhydrous sodium sulfate, filtered and concentrated under reduced pressure to give exclusively 3-(3-quinolyl) trans-2-propen-1-ol as a solid: 4.1 g, 81%.

Step (3)

Preparation of 3-(3-quinolyl)-2-propen-1-ol t-butyl carbonate (Scheme 1, Compound (I))

To a 500-mL three-necked round-bottom flask equipped with an overhead mechanical stirrer was charged 3-(3-quinolyl)-2-propen-1-ol (13.03 g, 70.43 mmol) as a mixture of cis- and trans-isomers (81% cis, and 19% trans), di-tert butyl dicarbonate (16.91 g, 77.48 mmol, 1.11 equiv), tetra n-butylammonium hydrogen sulfate (742 mg, 2.17 mmol) and methylene chloride (135 mL). The stirred mixture which resulted was cooled to 0 to 5° C. at which time aqueous 25% sodium hydroxide (33.3 mL) was added over 45 minutes such that the internal temperature did not rise above 20° C. Upon completion of the reaction (1 to 4 hours) as indicated by TLC (3:2 ethyl acetate/heptane), the reaction mixture was diluted with methylene chloride (50 mL) and washed with water (2×125 mL). The organic was dried over anhydrous sodium sulfate, filtered, and concentrated in vacuo to provide the 3-(3-quinolyl)-2-propen-1-ol-t-butyl carbonate: 18.35 g, 91.4% as an oil. This material can be further purified to remove lower R$_f$ impurities by eluting through a plug of silica gel with heptane/acetone/triethylamine (9:1:0.1). The product eluant is then concentrated under reduced pressure and further dried by the azeodistillation of ethyl acetate. This procedure provides the purified carbonate as a colorless oil which retains the original ratio of cis and trans isomers: 17.50 g, 87.2%.

Example 2

Preparation of 3-(3-Quinolyl)-2-Propen-1-ol t-Butyl Carbonate

Step (1)

Preparation of 3-(3-quinolyl)-2-propyn-1-ol t-butyl carbonate

To a dry 1-L three-necked round-bottom flask equipped with a nitrogen inlet and overhead stirrer was charged 3-(3-quinolyl)-2-propyn-1-ol (15.81 g, 86.39 mmol), di-tert-butyl dicarbonate (22.48 g, 103 mmol, 1.19 equiv), n-tetrabutyl ammonium hydrogen sulfate (0.86 g, 2.54 mmol, 0.029 equiv) and methylene chloride (300 mL). The resulting suspension was mechanically stirred while a 25% w/w aqueous NaOH solution (38 g) was added in over a period of 5 minutes. The biphasic mixture which resulted was stirred for 4 hours after which time the reaction was found to be complete by HPLC and TLC. The mixture was diluted with water (200 mL) and methylene chloride (100 mL). After stirring for 10 minutes and settling for 15 minutes the layers were separated. The organic layer was washed with water (1×200 mL) and 20% aq., NaCl (1×200 mL). The organic was then stirred with 15 g of sodium sulfate, filtered and then stripped to an oil under reduced pressure. The residual oil was taken up in isopropyl acetate/ hexane (1:1, 100 mL) and passed through a small pad of silica gel (8 g). The pad was rinsed with the same eluent (100 mL). The combined filtrates were concentrated under reduced pressure and rigorously dried in a vacuum oven to yield the 3-(3-quinolyl)-2-propyn-1ol t-butyl carbonate as a light orange-yellow colored oil: 24.50 g, 100%.

Step 2

Preparation of 3-(3-quinolyl)-2-propen-1-ol t-butyl carbonate (Compound (I))

To a 250 mL single-necked round-bottom flask was charged the 3-(3-quinolyl)-2-propyn-1-ol t-butyl carbonate (1.52 g, 5.37 mmol), isopropanol (30 mL) and 5% palladium on calcium carbonate poisoned with lead (Lindlar's catalyst, 75 mg, 0.049 equiv). The suspension was stirred (rapidly) magnetically and the atmosphere above the solution was purged with hydrogen. A balloon of hydrogen gas was then placed over the reaction stirring mixture and the reaction was allowed to stir for 16 hours at room temperature. The reaction mixture was then filtered through a 0.45μ filter disk and rinsed with 10 mL of isopropanol. The combined filtrates were concentrated under reduced pressure and the residue (1.55 g) was taken up in 9 mL of heptane/acetone (8:1) and eluted through a plug of silica gel (1.5 g) with 8:1:0.01 heptane/acetone/triethylamine. The desired fractions were combined and concentrated under reduced pressure to provide 3-(3-quinolyl)-2-propen-1-ol t-butyl carbonate: 1.1 g, 71.9%

Example 3

Preparation of 3-(3-Quinolyl)-2-Propen-1-ol t-Butyl Carbonate

Step (1)

Preparation of 3-(3-quinolyl)-2-propyn-1-ol

A 1-L three-necked round-bottom flask was charged with 37.2 g tetra-n-butyl ammonium bromide, 19.62 g palladium on carbon (5% loading, 50% wet with water), and 3.60 g of triphenylphosphine. The flask was fitted with a reflux condenser, a thermometer, a pressure equalizing addition funnel and a nitrogen inlet adapter. The solids were degassed by application of vacuum to the flask and venting with nitrogen (process repeated 3 times). Piperidine (69.0 g), acetonitrile (132 g) and 3-bromoquinoline (48.0 g) were added and the reaction mixture heated to 50° C. Propargyl alcohol (22.8 g) was added dropwise over 15 minutes, with no appreciable exotherm being observed. The reaction mixture was stirred at 50° C. until HPLC monitoring revealed the reaction to be complete (about 8 hours).

Once complete, the reaction mixture was hot-filtered (to remove the catalyst) through a ½" plug of filtrol filtering aid. The collected solids were washed with 50 mL of isopropanol. The combined filtrates were slowly added to 1.5 L of rapidly stirring distilled deionized water. The mixing continued for 10 minutes past the completion of the addition and the solid product was collected by filtration. The filtered solids were washed twice with 150 mL of distilled deionized water and dried in vacuo (nitrogen purge, oven temperature below 50° C.) overnight affording 41.85 g (99% yield) of a brownish yellow solid. Measured potency 85% versus known standard.

Step (2)

Preparation of 3-(3-quinolyl)-2-propen-1-ol

The 3-(3-quinolyl)-2-propyn-1-ol from above is reduced to the alkenol by either the hydrogenation method (Example 1, Step (2A)), or Red-Al method (Example 2, Step (2B)).

Step (3)

Preparation of 3-(3-quinolyl)-2-propen-1-ol t-butyl carbonate

The alkenol from above is converted into the 3-(3-quinolyl)-2-propen-1-ol t-butyl carbonate in accordance with the method described in Example 1, Step (3).

Example 4

Preparation of cis-3-(3-Quinolyl)-2-Propen-1-ol t-Butyl Carbonate

Step (1)

Preparation of Cis-3-(3-Quinolyl)-2-propen-1-ol

To a dry 3000-mL three-necked jacketed flask, equipped with a thermocouple was charged 3-(3-quinolyl)-2-propyn-1-ol (76 g, 415.3 mmol) (Example 3, Step (1)), 5% Pd/CaCO$_3$ (1.52 g) and 3,6-dithia-1,8-octanediol (0.76 g). 3A Ethanol (1125 mL) was then charged and the mixture which resulted was vigorously stirred at ambient temperature (19° C.). The atmosphere above the mixture was purged with hydrogen and then evacuated. This purging and evacuating process was repeated twice. Hydrogen balloons (0.32 psi) were placed above the reaction mixture and the progress of the reduction was monitored by HPLC analysis. After 25 hours, the reaction was stopped.

The mixture was filtered through a bed of diatomaceous earth and the flask and cake were washed with 3A ethanol. The filtrate was concentrated under reduced pressure. The residue was dissolved in methyl isobutyl ketone (MIBK, 400 mL) and this solution was passed through a plug of Filtrol (38 g). MIBK (125 mL) was used to rinse the flask and cake until the filtrate was colorless. The combined filtrates were concentrated to a volume of 200 mL then diluted with MIBK (270 mL) at which time the crystallization of the cis-PQ alcohol was initiated. The crystallizing solution was then slowly triturated with heptanes (270 mL) with stirring and later cooled to 0° C. overnight. The product was washed with cold MIBK/heptanes (3:4, 150 mL). The wet cake was vacuum oven dried at 50° C. for 6 hours to give cis-3-(3-quinolyl)-2-propen-1-ol (50.0 g, 70.0% yield, adjusted for potency of starting material). Purity as determined by HPLC was 98.9%.

Step (2)

Protection of cis-3-(3-quinolyl)-2-propen-1-ol

The solid cis-3-(3-quinolyl)-2-propen-1-ol (10.0 g, 54.1 mmol), di-tert-butyl dicarbonate (17.6 g, 80.6 mmol, 1.5 equiv), toluene (43 g) and tetra n-butylammonium hydrogen sulfate (0.68 g, 2.0 mmol) were combined and stirred (mechanically) in a three-necked round-bottom flask. To this stirring mixture was slowly added an aqueous sodium hydroxide solution (28 g H$_2$O and 7.0 g, NaOH) over 10 minutes. The temperature of the biphasic mixture warmed from 18° C. to 31° C. for 1.5 hours and then allowed to stir overnight at room temperature. The reaction was then diluted with toluene (33 mL) and water (19 mL). The layers were separated (aq. pH 12) and the organic was washed consecutively with water (1×28 mL) and 5% aq. NaCl (1×28 mL). The pH of the aqueous layers were 10 and 9 respectively. The organic was then washed with an aqueous sodium chloride solution (7 g NaCl, H$_2$O 28 g) before concentration under reduced pressure and a bath temperature of 50° C. The oil which resulted was chased with heptane (2×100 g). The residue was dissolved in 55 mL of heptane to initiate crystallization. This product was collected at −5° C., washed with cold heptane (10 mL) and vacuum dried at room temperature to provide a white to off white colored solid (13.6 g, 88.3%). Purity as determined by HPLC was 98.7%.

Example 5

Preparation of Cis-3-(3-Quinolyl)-2-Propen-1-ol t-Butyl Carbonate

To a 30 gallon reactor was charged 3-(3-quinolyl)-2-propyn-1-ol (5000 g, 27.3 mol) (Example 3, Step (1)), 5% Pd/CaCO$_3$—Pb (100 g) and 3,6-dithia-1,8-octanediol (50 g). The reactor was vented and purged with nitrogen three times before anhydrous ethanol (75 L, 60 kg) was charged. The mixture which resulted was stirred at 2 psi of hydrogen pressure and at a jacket temperature of 18° C. for 23 hours.

Upon reaction completion, the pressure was released and the reactor was vented and purged with nitrogen three times prior to filtration. The mixture was then filtered through a bed of celite. The reactor was splashed with 20 kg (25 L) of ethanol and passed through the filter also. The combined product filtrates were collected in a tared polylined drum and held for further processing.

To a 50 gallon reactor was charged tetrabutylammonium hydrogen sulfate (0.34 kg, 1.0 mol) and the ethanolic hydrogenation solution (27.3 mol). The ethanol was distilled off under vacuum and a jacket temperature of NMT 60° C. The residue was dissolved in toluene (25) and again concentrated under reduced pressure with a jacket temperature of NMT 65° C. The residue was again dissolved in toluene (18 kg) and analyzed by GC for the presence of ethanol. Di-tert-butyl dicarbonate (8.9 kg, 40.8 mol) and toluene (18 kg) was charged to the reactor and the internal temperature was raised to NMT 30° C. An aqueous sodium hydroxide solution (3.4 kg NaOH and 14 kg water) was then slowly charged to the reaction mixture maintaining an internal temperature of NMT 40° C. During the reaction, the biphasic suspension completely dissolved to give a clear amber colored solution. The reaction was allowed to proceed until determined by complete HPLC.

The solution was diluted with toluene (16.4 kg) and water (9.4 kg). The organic layer was separated and washed with water (2×14 kg) and 25% aq. sodium chloride (17.5 kg). The organic solution was then filtered through a bed of celite. The toluene product filtrate was distilled under vacuum and a jacket temperature of NMT 65° C. Toluene (14 kg) was charged back to dissolve the residue. The solution was then drained to clean and tared polypropylene carboy followed by a toluene rinse. The overall two step yield was 92%.

Example 6

Preparation of 3-(3-Quinolyl)-2-Propen-1-ol t-Butyl Carbonate

To a 100-mL round-bottom flask was charged the tetrahydropyranyl protected 3-(3-quinolyl)-2-propyn-1-ol (1.92 g, 7.19 mmol), Lindlar's catalyst (77 mg) and anhydrous ethanol (22 mL). The mixture which resulted was magnetically stirred under an atmosphere of hydrogen gas (balloon, 0.3 psi) for 46 hours. The reaction was tracked by HPLC and TLC and was terminated after partial conversion to the product (12% product, 88% starting material). The mixture was filtered to remove the catalyst and the filtrate was concentrated under reduced pressure to give an oil 1.95 g. The tetrahydropyranol protected 3-(3-quinolyl)-2-propen-1-ol was deprotected by standard methods and treated in accordance with the method described in Example 1, Step (1) to obtain the title compound.

Example 7

Preparation of 3-(3-Quinolyl)-2-Propen-1-ol t-Butyl Carbonate

Step (1)

Heck coupling of 3-bromoquinoline with acrolein diethylacetal (Scheme 4, Compound (9))

A mixture of 3-bromoquinoline (2 g, 9.6 mmol), acrolein diethylacetal (1.5 g, 11.5 mmol), tri(o-tolyl)phosphine (0.23 g, 0.76 mmol) and palladium acetate (43 mg, 0.2 mmol) in triethylamine (6 ml) was heated under nitrogen at 100° C. for 4 hours. TLC showed the reaction was complete. The crude product corresponded to Compound (8), of Scheme 4. After cooling to room temperature, the mixture was quenched with 15 ml of dilute HCl, and the product was extracted with 10 ml of methylene chloride. The organic layer was washed with 15 ml of water, filtered to remove insolubles and concentrated under vacuum to give a light brown oil (1.35 g). Column chromatography (silica gel, 20:80 ethyl acetate/hexane) gave 3-(3'-quinolyl)acrolein (0.75 g, 42.6%) (compound (9), Scheme 4) as light yellow crystals. MS(M+H$^+$)=184; H$^1$ NMR(ppm): 6.93 (1H, dd), 7.6 (1H, dd), 7.62 (1H, dd), 7.8 (1H, m), 7.9(1H, dd), 8.15 (1H, d), 8.32 (1H, d), 9.12 (1H, d), 9.8 (1H, d).

Step (2)

Reduction of 3-(3'-quinolyl)acrolein with borane t-butylamine (Scheme 4, Compound (6))

Borane t-butylamine (0.06 g, 0.7 mmol) was added to a stirred solution of 3-(3'-quinolyl)acrolein (0.32 g, 1.7 mmol) in tetrahydrofuran (10 ml) at room temperature. The mixture was stirred at room temperature for 90 minutes, quenched with 10 ml of water and extracted with 2×20 ml ethyl acetate. The organic layers were combined and washed with 10 ml of water and concentrated to give 3-(3'-quinolyl)allyl alcohol (0.3 g).

Step (3)

Preparation of 3-(3-quinolyl)-2-propen-1-ol t-butyl carbonate

The 3-(3'-quinolyl)allyl alcohol was treated in accordance with Step (3) of Example 1 to obtain the title compound.

Example 8

Preparation of 3-(3-Quinolyl)-2-Propen-1-ol t-Butyl Carbonate

Step (1)

Preparation of 3-(3-quinolyl)-2-propenoate (Scheme 4, Compound (11))

The 3-bromoquinoline (300 g, 1.44 mmol), ethyl acrylate (168 g, 1.68 mmol), palladium(II) acetate (32.3 g, 144 mmol), tetrabutylammonium bromide (478 g 1.44 mol), and sodium bicarbonate (483.9 g, 5.76 mol) were combined in a 5-L round-bottom flask with overhead stirring and 3 L dimethyl formamide (anhydrous). The reaction mixture was heated to 90° C. with heating mantle. After 30 minutes, 3-bromoquinoline was not detected by HPLC. The reaction was cooled to room temperature with an ice bath, and 2.65 L of ethyl acetate was added. The organic layer was washed with 1500 mL H$_2$O. The aqueous layer was extracted with 4×1 L of 1:1 toluene/ethyl acetate; the combined organic layers were then washed with 6×1 L brine, then evaporated to give 217.4 g (65% of desired product).

Step (2)

Preparation of 3-(3-quinolyl)-2-propen-1-ol (Scheme 4, Compound (6))

The 3-(3-quinolyl)-2-propenoate (141 g, 0.621 moles) was dissolved in 2.0 L anhydrous methylene chloride in a 5-L round-bottom flask with overhead stirring and cooled to −57° C. with isopropanol/dry ice bath. Diisobutylaluminum hydride (1.55 L, 1.0 M in methylene chloride) was added in a slow stream, keeping the temperature of the reaction mixture below −40° C. After 30 minutes, the starting ester is consumed. While cooling with dry ice/acetone, 434 mL MeOH was added dropwise and the mixture was allowed to warm to room temperature. Then, 2 L of 10% sodium potassium tartrate was added portionwise to the solution and the mixture was stirred for 1 h at room temperature. The layers were separated. The organic layer was washed with 2 L aq. NaCl solution and dried over $MgSO_4$. Evaporation gave a solid which was recrystallized from EtOAc to afford a yield of 71 g (62%) of a pinkish solid.

Step (3)

Preparation of 3-(3-quinolyl)-2-propen-1-ol t-butyl carbonate (Scheme 4, Compound (I))

Allylic alcohol (115.4 g, 623 mmol), di-tert-butyl dicarbonate (163.2 g, 748 mmol), and tetrabutylammonium hydrogen sulfate (6.35 g, 18.7 mmol) were combined in 721 mL methylene chloride, cooled to 0–5° C., and sodium hydroxide (92.7 g, 2.32 moles) in 293 mL $H_2O$ was added. The reaction was stirred under nitrogen and allowed to warm to r.t. overnight. The mixture was partitioned between $H_2O$ and methylene chloride (310 mL each). The aqueous layer was extracter with another 200 mL methylene chloride. The combined organic layers were washed with brine, dried with $Na_2SO_4$, filtered and evaporated to give 285.8 g of crude material which was purified by silica gel chromatography 20/80 ethyl acetate/hexanes to give 136.7 g (81%) of 3-(3-quinolyl)-2-propen-1-ol t-butyl carbonate.

Example 9

Preparation of 3-(3-Quinolyl)-2-Propen-1-ol t-Butyl Carbonate

To a 1-L three-necked round-bottom flask equipped with mechanical stirrer, J-Kem temperature probe, transfer cannula, and dry nitrogen line was charged 3-(3-quinolyl)-2-propenoate (18.78 g, 88.07 mmol, 1.0 equiv) and 370 mL (19.7 mL/g) of dry methylene chloride. The contents were mixed to dissolve and then cooled to −50±5° C. A solution of DIBAL in toluene (99.82 g of 25 wt. % solution; 25.0 g active DIBAL, 175.78 mmol, 2.00 equiv) was slowly charged over 2 hours, and the temperature was maintained at NMT −45° C. during the addition. An HPLC sample was taken at T=2 hours, and revealed that the reaction was complete.

The reaction was quenched by the slow addition of 19 mL of methanol, maintaining a temperature of NMT −30° C. This was followed by a charge of 200 mL of a 15% solution of potassium sodium tartarate, again maintaining a temperature of NMT −30° C. during the addition. The reaction mixture was then warmed to 0° C. and stirred at temperature for 1 hour. The cooling bath was removed and the reaction mixture was allowed to warm to room temperature with stirring overnight. The following morning the aqueous phase was removed and discarded. The organic phase was washed 2×95 mL with water.

The combined organic phases were cooled to 0 to 5° C. then 25.0 g of BOC (t-butyloxy-carbonyl) anhydride was added, followed by 1.2 g of tetrabutylammonium hydrogen sulfate, and 55 mL of 25% aqueous sodium hydroxide. The cooling bath was removed and the reaction mixture was allowed to warm to room temperature, with stirring, overnight. HPLC at T=16.5 hours revealed 2.2% remaining starting material. An additional 3.8 g of BOC anhydride was charged. A resample at T=19.5 hours reveals 0.8% remaining starting material. The reaction was considered to be complete. The reaction mixture was filtered, and the aqueous phase was separated and discarded. The organic phase was washed 2×95 mL with water, then filtered through a 18.7 g pad of flash grade silica. The silica pad was washed 1×100 mL with fresh methylene chloride. The crude carbonate was concentrated by rotary evaporation. After chasing the resultant thick brown oil with 75 mL of heptane, the residue was crystallized from 95 mL of heptane. The resultant slurry was cooled to 0 to 5° C., held at temperature for NLT 1 hour, thinned by the addition of an additional 25 mL of heptane, then filtered. The wetcake was washed with 25 mL with fresh cold heptane, then dried in a vacuum dessicator overnight.

The dried material weighed 11.09 g (68.0% yield). HPLC purity was 98.3%.

Example 10

Preparation of 3-(3-Quinolyl)-2-Propen-1-ol t-Butyl Carbonate

To a 1-L three-neck round-bottom flask equipped with mechanical stirrer, J-Kem temperature probe, transfer cannula, and dry nitrogen line was charged 3-(3-quinolyl)-2-propenoate (18.78 g, 88.07 mmol, 1.0 equiv) and 280 mL (15 mL/g) of dry THF. The contents were mixed to dissolve and then cooled to −50±5° C. A solution of DIBAL in toluene (102.02 g of 25 wt % solution; 25.5 g active DIBAL, 179.3 3 mmol, 2.03 equiv) was slowly charged over 2 hours, and the temperature was maintained at NMT −45° C. during the addition. Once the addition was complete the reaction mixture was warmed to −30±5° C. An HPLC sample was taken at T=3 hours, and revealed that the reaction was complete.

The reaction was quenched by the slow addition of 50 mL of cold tap water, maintaining a temperature of NMT −30° C. The reaction mixture was then warmed to 0° C. and stirred at temperature for NLT 2 hours. The cooling bath was removed and the reaction mixture was allowed to warm to room temperature with stirring overnight.

The following morning the reaction mixture was filtered to remove the precipitated aluminum salts. The salts were washed with an additional 2×100 mL of fresh THF. The combined organic phases were cooled to 0 to 5° C. then 20.0 g of BOC anhydride was added, followed by 1.1 g of tetrabutylammonium hydrogen sulfate, and 55 mL of 25% aqueous sodium hydroxide. HPLC at T=4.74 hours revealed 8.8% remaining starting material. An additional 6.0 g of BOC anhydride was charged, along with 10 mL of 25% aqueous sodium hydroxide. The reaction mixture was then stirred at room temperature overnight.

The following morning HPLC analysis revealed starting material was still present. Additional BOC anhydride (16.0 grams) and sodium hydroxide solution (20 mL) was needed to push the reaction to completion (T=29.5 hours).

The crude reaction mixture was filtered to remove solids, and the remaining organic phase was washed 2×50 mL with water and 1×50 mL with brine. The aqueous phases were then back extracted with 50 mL of toluene. The combined organic phases were concentrated to a thick oil. After chasing the resultant thick brown oil with 75 mL of heptane, the residue was crystallized from 75 mL of heptane. The resultant slurry was cooled to 0 to 5° C., held at temperature for NLT one hour, thinned by the addition of an additional 25 mL of heptane, then filtered. The wetcake was washed with 25 mL with fresh cold heptane, then dried in a vacuum dessicator overnight.

The dried material weighed 16.74 g (66.6% yield). HPLC purity was 98.9%.

Example 11

Preparation of 3-(3-Quinolyl)-2-Propen-1-ol t-Butyl Carbonate

Step (1)

Preparation of 3-(3'-quinolyl)-2-propenoic acid (Scheme 4, Compound (12))

Methyl 3-(3' quinolyl)-2-propenoate (25 g, 117 mmol) (Scheme 4, Compound (11)); see Example 8, Step (1) for preparation) and methanol (125 mL) were charge to a three-necked round-bottom flask equipped with an overhead stirrer. Sodium hydroxide (23.5 g, 588 mmol) was dissolved in water (50 mL) and added to the suspension to provide a homogeneous solution. The reaction was stirred for 1–3 hours prior to adding additional water (250 mL). Concentrated hydrochloric acid was then added in batches until the solution was slightly acidic (55–60 mL, 12 N). This resulted in the precipitation of a white solid. The solid was isolated by filtration and washed with water and methanol. The white, crystalline product was then dried in a vacuum oven at ambient temperature. Isolated yields ranged from 20 g, 86% to 22.2 g, 95%.

Step (2)

Preparation of 3-(3-quinolyl)-2-propen-1-ol (Scheme 4, Compound (6))

3-(3'-Quinolyl)-2-propenoic acid (2.5 g, 12.5 mmol) and tetrahydrofuran (50 mL) were charged to a round-bottom flask equipped with a temperature probe and magnetic stirrer. The suspension was cooled to 0° C. and 4-methylmorpholine (1.93 g, 1.9 mmol) was added rapidly followed by slow addition of isobutylchloroformate (1.93 g, 14 mmol) over 30 minutes maintaining an internal temperature less than 5° C. The mixture was then stirred at 0° C. for an additional hour and then filtered into water (7.5 mL) which was cooled to 0° C. The light yellow solution was kept at 0° C. and the sodium borohydride (1 g, 26.5 mmol) was added in batches over 45 minutes to maintain a temperature below 5° C. Following addition, the reaction was stirred an additional 1.5 hours at 0° C.

The reaction was quenched with slow addition 3 N HCl (40 mL) at 0° C. The resulting orange-red solution was extracted with ethyl acetate (50 mL) to remove some impurities. The acidic aqueous layer, which contained the product, was neutralized with saturated sodium bicarbonate solution and extracted with ethyl acetate (4×50 mL). The combine organic extracts were dried with magnesium sulfate and filtered though a plug of silica gel to remove some of the red color. The resulting light yellow liquid was concentrated to give the crude alcohol as an orange-red oil (1.87 g, 10.1 mmol, 81% yield, HPLC purity 90%).

Step (3)

Preparation of 3-(3-quinolyl)-2-propen-1-ol t-butyl carbonate

The 3-(3-quinolyl)-2-propen-1-ol was treated in accordance with Step (3) of Example 1 to obtain the desired t-butyl carbonate.

Examples 12–16

Examples 12–16 relate to methods for preparing 1-(3-quinolyl)-2-propen-1-ol t-butyl carbonate.

Example 12

Preparation of 1-(3-Quinolyl)-2-Propen-1-ol t-Butyl Carbonate via 2-Iodo-3-Quinoline Carboxaldehyde (Scheme 5, Compound (II))

Step (1)

Preparation of 2-iodo-3-quinoline carboxaldehyde (Scheme 5, Compound (13))

To a dry three-necked round-bottom flask equipped with nitrogen inlet and overhead stirrer, reflux condenser was charged 2-chloro-3-quinolinecarboxaldehyde (20 g, 104 mmol) and $CH_3CN$ (200 ml) followed by sodium iodide (39 g, 260 mmol) and conc. HCl (cat, 4 ml) and the solution was heated to reflux for 6 h. The reaction mixture was evaporated to about ½ the volume, poured onto water (250 ml) and saturated sodium carbonate (100 ml). The iodo derivative crystallises out and it was filtered and dried under vacuum at 40° C. for 48 hrs.

Yield=21 g (71%).

Step (2)

Preparation of 1-(3-quinolyl)-2-propen-1-ol t-butyl carbonate

To a solution of 2-iodo-3-quinoline carboxaldehyde (3 g, 10.6 mmol) in THF (25 ml) at –5° C., vinylmagnesium bromide (1 M solution, 10.8 ml, 10.8 mmol) was added. It was stirred at that temperature until the starting material disappears, which takes about one hour. N-butyllithium (8.5 ml, 2.5 M soln, 21.2 mmol) was added and the solution was stirred for another 25 min and then quenched with t-butanol (1.63 g, 22 mmol, only the C-2 anion is being quenched). Then a solution of di-tert-butyl dicarbonate (2.54 g, 11.6 mmol) was added and the solution was stirred for 2 h at –5° C. The reaction was then worked up with MTBE (60 ml) and 10% ammonium chloride solution (25 ml). The organic layer washed again with saturated NaCl solution and it was concentrated to an orange oil which crystallised on standing at 0° C. overnight. It was used as such for alkylation experiments. Yield=2.8 g (92.7%)

Example 13

Preparation of 1-(3-Quinolyl)-2-Propen-1-ol t-Butyl Carbonate via Condensation with Ethynylmagnesium Chloride (Scheme 5, Compound (II))

Step (1)

Condensation of quinoline-3-carboxaldehyde with ethynylmagnesium chloride (Scheme 5, Compound (II), wherein $R^8$ is —C≡$CR^{11}$ and $R^{11}$ is hydrogen)

To a stirred slurry of quinoline-3-carboxaldehyde (5 g, 31.8 mmol) in tetrahydrofuran (15 ml) at –150° C., was added ethynylmagnesium chloride (66.8 ml, 33.4 mmol, 0.5M in THF) at –10 to –15° C. A clear solution which was formed after the addition was stirred at –15° C. for 30 minutes. HPLC showed reaction was complete. This was transferred by cannula to a stirred solution of di-tert-butyl dicarbonate (7.84 g, 41.3 mmol) in tetrahydrofuran (10 ml) at −10 to −15° C. The mixture was warmed to 10° C. in one hour. HPLC showed complete disappearance of the Grignard adduct. The reaction mixture was cooled to −50° C., diluted with 50 ml of methyl t-butyl ether and quenched with a solution of citric acid (8 g) in water (45 g) at <10° C. After 30 minutes mixing, the organic layer was washed with 60 ml of saturated sodium bicarbonate and 2×30 ml water. The organic solution was filtered through a bed of filter aids, and the filtrate was concentrated under vacuum to an oil. The oil was azeotropically dried with 2×50 ml of ethyl acetate to give the crude oil (10.4 g). Column chromatography (silica gel, 30:70 EtOAc/hexane) gave pure fraction of the desired product (8.65 g) as a very viscous light yellow oil. Yield was 96.1%. MS(m/z)284(M+H). $H^1$ NMR (ppm, $CDCl_3$): 9.08 (d, 1H), 8.35 (d, 1H), 8.12 (dd, 1H), 7.87 (dd, 1H), 7.75 (m, 1H), 7.58 (m, 1H), 7.47 (d, 1H), 2.82 (d, 1H), 1.50 (s, 9H).

Step (2)

Preparation of 1-(3-quinolyl)-2-propen-1-ol t-butyl carbonate (Scheme 5, Compound (II), wherein $R^8$ is —CH=$CHR^{11}$ and $R^{11}$ is hydrogen)

A solution of 1-(3-quinolyl)-2-propyn-1-ol t-butyl carbonate (1.5 g, 5.3 mmol) in isopropanol (30 ml) was degassed and nitrogen purged twice. 5% palladium on calcium carbonate poisoned with lead (Lindlar's catalyst, (0.11 g, 0.05 mmol) was added. The mixture was again evacuated twice, and a hydrogen balloon was placed over the flask with vigorous stirring at room temperature overnight. HPLC showed reaction was complete, and the catalyst was filtered off. The filtrate was concentrated under vacuum to give an oil (1.57 g). The oil was purified by column chromatography (silica gel, 30:70 EtOAc/hexane) to give the pure product (1.41 g). Yield was 93.3%. MS(m/z) 286(M+H)$^+$. $H^1$ NMR (ppm, $CDCl_3$): 8.94 (d, 1H), 8.15 (d, 1H), 8.11 (d, 1H) 7.80 (dd, 1H), 7.70 (m, 1H), 7.52 (m, 1H), 6.27 (s, 1H), 6.05–6.18 (m, 2H), 5.30–5.45 (m, 2H), 1.50 (s, 9H).

Example 14

Preparation of 1-(3-Quinolyl)-2-Propen-1-ol t-Butyl Carbonate via Condensation with Ethynylmagnesium Bromide (Scheme 5, Compound (II))

To a stirred solution of quinoline-3-carboxaldehyde (5 g, 31.8 mmol) in tetrahydrofuran (15 ml) at −15° C. was added ethynylmagnesium bromide (66.8 ml, 0.5M in THF) at −10 to −15° C. The reaction was complete after 50 minutes by HPLC. This solution was transferred to a stirred solution of di-tert-butyl dicarbonate (7.84 g, 35.9 mmol) in THF (10 ml) at −10 to −15° C. After the transfer, the mixture was warmed to room temperature. Reaction was determined to be complete at 3 hours by HPLC. The mixture was cooled back down to −50° C., diluted with 50 ml of methyl t-butyl ether and quenched with a solution of citric acid (8 g) in water (45 ml) at <10° C. The organic layer was washed with 60 ml of saturated sodium bicarbonate and 200 ml water. After filtration, the organic layer was concentrated to dryness, azeotropically dried with 2×50 ml ethyl acetate to give a brown oil (9.5 g). Column chromatography (silica gel, 30:70 EtOAc/hexane) gave pure product (8.45 g). Yield was 93.4%.

The product obtained from this reaction is identical to that from ethynylmagnesium chloride. The product can be reduced to provide the 1-(3-quinolyl)-2-propen-1-ol t-butyl carbonate by methods described in Example 13, Step (2).

Example 15

Preparation of 1-(3-Quinolyl)-2-Propen-1-ol t-Butyl Carbonate via Condensation with Vinylmagnesium Chloride (Scheme 5, Compound (II))

To a stirred solution of quinoline-3-carboxaldehyde (3 g, 19.1 mmol) in tetrahydrofuran (15 ml) at −10° C., was added vinylmagnesium chloride solution in THF (11.3 ml, 15 wt. %, d=0.975 g/mL) at −5 to −10° C. At the end of the addition, HPLC showed reaction was complete. This brown solution was transferred by cannula to a stirred solution of di-tert-butyl dicarbonate (4.4 g, 22.9 mmol) in THF (10 ml) at −10 to −15° C. After the transfer, the reaction was warmed to 0–5° C. for 1 hour. The mixture was cooled back down to −10° C., diluted with 60 ml of methyl t-butyl ether and quenched with a solution of citric acid (4.8 g, 22.9 mmol) in water (27 ml) at <5° C. After 5 hours mixing, the organic layer was separated, washed with 30 ml of 7% sodium bicarbonate. 2×30 ml water, filtered and the filtrate was concentrated under vacuum to a light brown oil (5.5 g). Column chromatography (silica gel, 20:80 EtOAc/hexane) of the crude product gave pure carbonate (4.3 g). Yield was 79.0%.

Spectral data of this material are consistent with that obtained by reduction of the ethynyl carbonate.

Example 16

Preparation of 1-(3-Quinolyl)-2-Propen-1-ol t-Butyl Carbonate via Condensation with Vinylmagnesium Bromide (Scheme 5, Compound (II))

A solution of quinoline-3-carboxaldehyde (2 g, 12.7 mmol) in THF (10 ml) was cooled to −20° C., and 1 M vinylmagnesium bromide (12.7 ml, 12.7 mmol) was added at −15 to −20° C. At the end of the addition, reaction was complete. This brown solution was transferred to a solution of di-tert-butyl dicarbonate (3.6 g, 16.5 mmol) in THF (10 ml) at −30° C. The solution was gradually warmed to room temperature and stirred for 2 hours. The mixture was cooled back down to −50° C., and quenched with a solution of citric acid (3.2 g) in 18 g water at −5 to 5° C. After one hour stirring, the organic layer was washed with 20 ml of 7% sodium bicarbonate and 2×20 ml water. The organic layer was concentrated to dryness and chromatographed by silica gel column to give the pure product (2.1 g). Yield was 57.9%.

Examples 17–20

Examples 17–20 illustrate methods for preparing a quinoline-3-carboxaldehyde, which can be used as an intermediate in the synthesis of carbonate or carbamate compounds of general formula (I), (II) or (III). The prepared quinoline-3-carboxaldehyde is treated according to syntheses described in Schemes 5 and 7 as detailed by the description and Examples herein to provide the desired carbonate or carbamate compounds.

Example 17

Preparation of Quinoline-3–Carboxaldehyde

Step 1

Preparation of 2-chloro-quinoline-3-carboxaldehyde dimethylacetal (Scheme 6, Compound (16))

To a 250-mL three-necked round-bottom flask equipped with mechanical stirrer, temperature controller, heating mantle, reflux condenser and dry nitrogen line was charged quinoline-2-chloro-3-carboxaldehyde (11.7 g, 61.06 mmol) and 120 mL of methanol. The reaction was heated under reflux for one hour. The reaction was monitored by thin layer chromatography (40:60 ethyl acetate/heptane), which showed conversion to the acetal was complete after one hour. The product solution was used directly for dehalogenation in Step 2.

Step 2

Preparation of quinoline-3-carboxaldehyde dimethylacetal (Scheme 6, Compound (17))

A solution of 2-chloro-quinoline-3-carboxaldehyde dimethylacetal was charged to a second vessel containing 0.7 g of 10% Pd on carbon (50% wet) and potassium carbonate (12.5 g, 90.44 mmol). The reaction vessel was evacuated then filled with hydrogen gas (3×) at 1 atmosphere. After completion of the reaction, the catalyst was removed by filtration and washed with methanol. The solvent was removed by rotary evaporation. The oily residue was dissolved in 120 mL of isopropyl acetate and washed 3 times with 60 mL of water. The organic phase was then concentrated to an oil by rotary evaporation to afford the product as an oil (12.4 g, 100%). MS: M/Z 204 (M+H$^+$); $^1$H NMR (CDCl$_3$, δ) 3.40 (s, 6H), 5.65 (broad s, 1H), 7.55 (m, 1H), 7.73 (m, 1H), 7.86 (dd, 1H), 8.13 (d, 1H), 8.25 (d, 1H), 8.99 (d, 1H).

Step 3

Preparation of quinoline-3-carboxaldehyde (Compound (15))

To a 250-mL three-necked round-bottom flask equipped with magnetic stirring, temperature controller, heating mantle, reflux condenser and dry nitrogen line was charged 4.5 g of crude acetal, 30 mL of isopropanol, and 22 mL of 88% formic acid. This mixture was heated under reflux and monitored by thin layer chromatography (40:60 ethyl acetate/heptane). After completion of the reaction, the mixture was concentrated by rotary evaporation. The residue was partitioned between 50 mL portions of ethyl acetate and 5% sodium bicarbonate. After discarding the aqueous phase, the organic phase was washed 1×50 mL with water. The organic phase was then concentrated to an oil by rotary evaporation. The crude product was dissolved in hot heptane, filtered through celite to remove a small amount of oily residue, then concentrated to a light yellow solid by rotary evaporation (86%). MS: M/Z 158 (M+H$^+$); $^1$H NMR (CDCl$_3$, δ) 7.68 (m, 1H), 7.90 (m, 1H), 8.0 (dd, 1H), 8.20 (dd, 1H), 8.64 (d, 1H), 9.48 (d, 1H), 10.26 (s, 1H).

Example 18

Preparation of Quinoline-3–Carboxaldehyde

Step (1)

Quinoline-2-chloro-3-carboxaldehyde dimethylacetal (Scheme 6, Compound (16))

To a stirred solution of quinoline-2-chloro-3-carboxaldehyde (5 g, 26 mmol) in methanol (150 ml) at room temperature, was bubbled in hydrochloric acid gas (1.7 g, 46.6 mmol). The solution was stirred at room temperature for 25 minutes. Reaction was complete by HPLC. NaHCO$_3$ (4.7 g, 56 mmol) was added to the reaction flask in portions and stirred for 10 additional minutes. The solid precipitate was filtered off, the filtrate was concentrated on a rotary evaporator to give an oil. The oil was redissolved in ethyl acetate (75 ml), washed with H$_2$O (30 ml) and concentrated to the product as an oil (6.2 g, 100%). MS: M/Z 238 (M+H$^+$); $^1$H NMR (CDCl$_3$, δ) 3.45 (s, 6H), 5.72 (d, 1H), 7.58 (m, 1H), 7.75 (m, 1H), 7.85 (dd, 1H), 8.25 (dd, 1H), 8.42 (s, 1H); $^{13}$C NMR (δ) 54, 100.4, 126.8, 127.3, 128.1, 128.2, 129.2,130.0, 137.2, 147.4, 149.3.

Step (2)

Preparation of quinoline-3-carboxaldehyde

The quinoline-2-chloro-3-carboxaldehyde dimethylacetal from above was treated in accordance Steps (2) and (3) of Example 17 to obtain quinoline-3-carboxaldehyde.

Example 19

Preparation of Quinoline-3-Carboxaldehyde

Step (1)

Preparation of quinoline-3-carboxaldehyde dimethylacetal (Scheme 6, Compound (16))

A mixture of quinoline-2-chloro-3-carboxaldehyde acetal (0.8 g, 3.4 mmol), triethylamine (0.69 g, 6.8 mmol) and 10% palladium on carbon (0.05 g, 50% wet) in methanol (15 ml) was nitrogen purged and evacuated. A hydrogen balloon was placed over the reaction flask, and the mixture was vigorously stirred at room temperature for 15 h. HPLC showed no starting material was left. The resulting mixture was degassed and nitrogen purged twice. The catalyst was filtered off and rinsed with methanol. The filtrate and the rinse were combined, and concentrated to an oil. The oil was dissolved in ethyl acetate (25 ml) and washed with water (20 ml). The ethyl acetate layer was concentrated to an oil which was purified by column chromatography (30:70 EtOAc/hexane) to give pure quinoline-3-carboxaldehyde dimethylacetal (0.55 g, 80.4%).

Step (2)

Preparation of quinoline-3-carboxaldehyde

The quinoline-3-carboxaldehyde dimethylacetal from above was treated in accordance with Step (3) of Example 8 to obtain quinoline-3-carboxaldehyde.

Example 20

Preparation of Quinoline-3-Carboxaldehyde

Step (1)

Preparation of quinoline-3-carboxaldehyde dimethylacetal (Scheme 6, Compound (16))

Quinoline-2-chloro-3-carboxaldehyde (1.0 g, 5.2 mmol) was dissolved in methanol (20 ml) and refluxed for 1.5 h. To this solution was added 10% palladium on carbon (100 mg) and ammonium formate (1.65 g, 26 mmol) and refluxed for two hours to form quinoline-3-carboxaldehyde dimethylacetal (>99%).

Step (2)

Preparation of quinoline-3-carboxaldehyde

The quinoline-3-carboxaldehyde dimethylacetal from above was treated in accordance with Step (3) of Example 8 to obtain quinoline-3-carboxaldehyde.

Examples 21–22

Examples 21–22 illustrate methods for preparing derivatives of formula (I) from quinoline-3-carboxaldehyde.

Example 21

Preparation of 3-(3-Quinolyl)-2-Propen-1-ol t-Butyl Carbonate via Condensation of Quinoline-3-Carboxaldehyde with Ethyl Acetate (Scheme 7, Compound (II))

Step (1)

Condensation of quinoline-3-carboxaldehyde with ethyl acetate

To a 50-mL round-bottom flask equipped with magnetic stirring and a dry nitrogen line was added 1.1 g (7.0 mmol=1.0 equiv) of quinoline-3-carboxaldehyde and 11.0 mL of ethyl acetate. This was mixed to dissolve and the resultant solution was cooled to 0–5° C. in an ice/water bath.

To this solution was charged 1.03 g (8.4 mmol=1.2 equiv) of potassium t-butoxide in a single portion. Continue stirring the mixture at 0–5° C. TLC at t=2 hr. revealed that the reaction was complete. Acetic acid (506 mg=8.4 mmol=1.2 equiv) was then charged to neutralize the base. This mixture was then washed with 5% sodium bicarbonate solution until the aqueous phase remained basic. The mixture was diluted with ethyl acetate as needed to assist in the washing. The organic phase was then concentrated by rotary evaporation to yield 1.1 g of crude product. The crude material can be recrystallized from 10% ethyl acetate/heptane.

Step (2)

Preparation of 3-(3-quinolyl)-2-propen-1-ol t-butyl carbonate

The ethyl 3-(3-quinolyl)-2-propenoate was treated in accordance with Steps (1) –(3), Example 7 to obtain 3-(3-quinolyl)-2-propen-1-ol t-butyl carbonate.

Example 22

Preparation of 3-(3-Quinolyl)-2-Propen-1-ol t-Butyl Carbonate via Condensation of Quinoline-3–Carboxaldehyde Step (1)

Preparation of 3-(3-quinolyl)propenal (Scheme 7, Compound (9))

To a 500-mL round-bottom flask, equipped with mechanical stirrer, dropping funnel and temperature bath was charged 30.9 g (0.2 mol) quinoline 3-carboxaldehyde and acetaldehyde (50 mL). The mixture was cooled to –10° C. and a solution of sodium hydroxide (500 mg) in methanol (8 mL) was added dropwise keeping the temperature below 10° C. The mixture was stirred at 0° C. for 30 min. Acetic anhydride (50 mL) was added and the mixture was heated to 70° C. (methyl acetate formed in the reaction was removed). After 1 hour, the mixture was cooled to 30° C. and 100 mL 3N HCl (50 mL conc. HCl in 100 mL water) was added. The mixture was heated to 80° C. for 45 min. and neutralized with 10% sodium carbonate solution. (The organic layer, containing product, was checked by TLC, system isopropyl acetate, visualize under short UV). At the end of the reaction, the mixture was cooled to <30° C., diluted with 200 mL water and it was washed with 2×150 mL isopropyl acetate. To the aqueous layer was then added isopropyl acetate (500 mL) and the pH was brought to >8 by neutralization with sodium carbonate. The organic layer was separated and concentrated to a small volume until the product starts to crystallize. The mixture was stirred for 30 min. filtered and dried to give 18.5 g product as a light yellow solid. A second crop (5.4 g) was collected by concentration of the mother liquor and filtration of the solid product followed by washing with MTBE (25 mL). Total yield, 23.9 g (66%). The NMR of the product was consistent with the proposed structure.

Step (2)

Preparation of 3-(3-quinolyl)-2-propen-1-ol (Scheme 7, Compound (3))

A mixture of 3-(3-quinolyl)l)propenal (10 g, 54.6 mmol) in methanol (50 mL) was cooled to 0° C. and to this mixture, sodium borohydride (1.03 g, 27 mmol) was charged in small portions keeping the temperature below 10° C. After the addition was complete, the mixture was stirred at 23° C. for 90 min. until the reaction was complete as monitored by TLC (isopropyl acetate, visualize under uv). To the mixture, saturated ammonium chloride solution (20 mL) was added and the mixture was stirred for one hour. The mixture was then concentrated under vacuum at 45° C. to remove methanol. The product was extracted in isopropyl acetate (150 mL), and the solvent was evaporated under vacuum to dryness. The product was; triturated with MTBE (40 mL), filtered, washed with MTBE (10 mL) and dried to give 3-(3-quinolyl)-2-propen-1-ol (6.6 g, 65.4%) as a light yellow solid. The NMR of the product was consistent with the proposed structure.

Examples 23–27

Examples 23–27 relate to methods for preparing a carbamate derivatives of the general formula (I). The 3-(3-quinolyl)-2-propyn-1-ol derivatives can be used to obtain the propenyl carbamate derivatives of the general formula.

Example 23

Preparation of 3-(3-Quinolyl)-2-Propyn-1-ol Dicyclohexyl Carbamate (Scheme 1, Compound (I))

To a dry three-necked round-bottom flask equipped with nitrogen inlet and overhead stirrer was charged 3-(3-quinolyl)-2-propyn-1-ol (1 g, 5.4 mmol) in THF (10 ml) and the solution was cooled to 0° C. Potassium t-butoxide (0.67 g, 5.9 mmol) was then added followed by dicyclohexylcarbamoyl chloride (1.32 g, 5.4 mmol). The mixture was stirred for 2 hours at 0° C. and then allowed to warm up to room temperature over a period of 6 hours by which time the reaction was determined to be complete. The reaction mixture was worked up with MTBE (50 ml) and 10% NH$_4$Cl (25 ml) and the organic layers were concentrated to an oil. The purity compared to the standard was 94% and was used as such. Yield=2 g (95%).

Example 24

Preparation of 3-(3-Quinolyl)-2-Propyn-1-ol Diphenyl Carbamate (Scheme 1, Compound (I))

To a dry three-necked round-bottom flask equipped with nitrogen inlet and overhead stirrer was charged 3-(3- quinolyl)-2-propyn-1-ol (5 g, 27 mmol) in THF (50 ml) and the solution was cooled to 0° C. Potassium t-butoxide (3.6 g, 32 mmol) was then added followed by diphenylcarbamoyl chloride (6.9 g, 29.7 mmol). The mixture was stirred for 2 hours at 0° C. and then allowed to warm up to room temperature over a period of 6 hours by which time the reaction was determined to be complete. The reaction mixture was worked up with MTBE (100 ml) and 10% NH$_4$Cl (50 ml) and was concentrated to ¼ the volume. Heptane (75 ml) was added and the product was crystallised out. Yield= 8.3 g (80%).

Example 25

Preparation of 3-(3-Quinolyl)-2-Propyn-1-ol Diisopropyl Carbamate (Scheme 1, Compound (I))

To a dry three-necked round-bottom flask equipped with nitrogen inlet and overhead stirrer was charged 3-(3-quinolyl)-2-propyn-1-ol (2 g, 10.8 mmol) (Scheme 1, Compound (3) in THF (20 ml) and the solution was cooled to 0° C. Potassium t-butoxide (1.34 g, 11.9 mmol) was then added followed by diisopropylcarbamoyl chloride (1.65 g, 11.9 mmol). The mixture was stirred for 2 h at 0° C. and then allowed to warm up to room temperature over a period of 6 hours, by which time the reaction was determined to be complete. The reaction mixture was worked up with MTBE (50 ml) and 10% NH$_4$Cl (25 ml) and was concentrated to an orange oil. Yield=3.3 g (100%)

Example 26

Preparation of 3-(3-Quinolyl)-2-Propyn-1-ol Morpholine Carbamate (Scheme 1, Compound (I))

To a dry three-necked round-bottom flask equipped with nitrogen inlet and overhead stirrer was charged 3-(3-quinolyl)-2-propyn-1-ol (2 g, 10.8 mmol) (Scheme 1, Compound (3) in THF (20 ml) and the solution was cooled to 0° C. Potassium t-butoxide (1.34 g, 11.9 mmol) was then added followed by morpholine acid chloride (1.95 g, 13 mmol). The mixture was stirred for 2 hours at 0° C. and then allowed to warm up to room temperature over a period of 6 hours by which time the reaction was determined to be complete. The reaction mixture was; worked up with MTBE (50 ml) and 10% NH$_4$Cl (25 ml), concentrated to an orange oil, and purified by column chromatography using heptane and ethyl acetate as eluant. A total of 1.4 g was obtained as pure fraction (100%). Yield=1.4 g (44%)

Example 27

Preparation of 3-(3-Quinolyl)-2-Propen-1-ol Imidazole Carbamate (Scheme 1, Compound (I))

To a dry three-necked round-bottom flask equipped with nitrogen inlet and overhead stirrer was charged 3-(3-quinolyl)-2-propen-1-ol (5 g, 27 mmol) (Scheme 1, Compound (3) in CH$_2$Cl$_2$ (50 ml) and carbonyldiimidazole (4.82 g, 29.7 mmol) was added and the mixture was stirred at room temperature for 8 h. The reaction mixture was worked up by quenching with 10% NH$_4$Cl (25 ml) and concentrated ¼ the volume. Heptane (50 ml) was added and the product crystallised out. Yield=7.2 g (95.5%)

Example 28

Examples 28 illustrates a method for preparing an allyl carbonate compound of the general formula (I).

Example 28

Preparation of Allyl t-Butyl Carbonate

A 3-L three-necked round-bottom flask equipped with mechanical stirring, a nitrogen inlet adapter and a pressure equalizing addition funnel was charged with allyl alcohol (149.5 g, 2.57 mol), di-tert-butyl dicarbonate (510 g, 2.34 mol), and CH$_2$Cl$_2$ (1200 mL) and cooled to 0° C. A 0° C. solution of 30% NaOH (aq.) (1000 mL, 7.5 mol, 3.2 equiv) was added dropwise to the rapidly stirring solution at such a rate that the internal temperature did not rise above 20° C. (about 1 hour). The reaction mixture was stirred at 20° C. for 2 hours prior to workup.

The crude reaction mixture was partitioned between 1 L water and 500 mL CH$_2$Cl$_2$. The organic layer was separated, washed with 1 L water and 1 L saturated NaCl solution, dried over MgSO$_4$, filtered and reduced to dryness in-vacuo, to afford about 300 g of a yellow oil. The crude product was purified by fractional distillation, b.p. 96° C. at 70 mmHg, affording the product as a colorless oil, 250.3 g (68%). The product had a b.p. of 96° C. at 70 mmHg. $^1$H NMR (CDCl$_3$, 300 MHz): d 5.95 (m, 1H), 5.3 (appar quartet of quartets, 2H), 4.55 (appar doublet of triplets, 2H), 1.49 (s, 9H). $^{13}$C NMR (CDCl$_3$, 75 MHz): d 153.1, 131.9, 118.3, 81.9, 67.4, 27.6. MS (NH$_3$, CI): 176 (M+NH$_4$)$^+$. Anal Calc'd for C$_8$H$_{14}$O$_3$: C, 60.73; H, 8.92. Found: C, 60.95; H, 8.96.

What is claimed is:
1. A compound having the formula

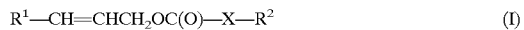

$$R^1\text{---}CH\text{=}CHCH_2OC(O)\text{---}X\text{---}R^2 \quad (I)$$

wherein
X is —O— or —NR$^3$—;
R$^1$ is quinolyl optionally substituted with one or more substituents selected from:
(i) alkyl,
(ii) alkoxy,
(iii) aryl,
(iv) nitro, and
(v) halo;
R$^2$ is C$_1$–C$_{10}$-alkyl; and
R$^3$ is hydrogen or C$_1$–C$_6$-alkyl; or R$^2$ and R$^3$ taken together form an aromatic or non-aromatic ring.

2. The compound according to claim 1 wherein X is —O—.

3. The compound according to claim 2 wherein R$^1$ is quinolyl.

4. The compound according to claim 3 wherein R$^2$ is tert-butyl.

5. The compound 3-(3-quinolyl)-2-propen-1-ol-t-butyl carbonate.

* * * * *

UNITED STATES PATENT AND TRADEMARK OFFICE
CERTIFICATE OF CORRECTION

PATENT NO. : 6,579,986 B2
DATED : June 17, 2003
INVENTOR(S) : Michael S. Allen et al.

It is certified that error appears in the above-identified patent and that said Letters Patent is hereby corrected as shown below:

Column 8,
Line 2, replace the words "cis" and "trans"" with the italicized words -- cis -- and -- trans --.
Lines 29 and 43, replace "cis" with the italicized word -- cis --.
Line 47, replace "trans" with the italicized word -- trans --.

Column 9,
Lines 4 and 31, replace the words "cis" and "trans" with the italicized words -- cis -- and -- trans --.
Line 47, in the word "di-tert-butyl" italicized the word "tert"
Line 54, in the word "di-tert-bytyl" italicized the word "tert"

Column 10,
Line 40, replace "cis" with the italicized word -- cis --.
Line 59, in the word "di-tert-butyl" italicized the word "tert"

Column 21,
Line 7, replace "(cis)" with italicized -- (cis) --.
Line 27, replace "cis" with the italicized word -- cis --.
Line 28, replace "trans" with the italicized word -- trans --.
Line 29, replace "cis" with the italicized word -- trans --.
Line 30, in the word "cis-and trans-alkenols" italicized the words -- cis -- and -- trans --.
Line 31, replace "cis" with italicized the word --cis --.
Line 32, replace "trans" with italicized word -- trans --.
Line 37, 38 and 59, replace "trans" with italicized word -- trans --.

Column 22,
Line 2, in the phrase "as a mixture of cis-and trans-isomers (81% cis, and 19% trans)" italicized the words -- cis --, -- trans --, -- cis --, trans --.
Line 21, replace "cis" with italicized word -- cis --.
Line 22, replace "trans" with italicized word -- trans --.

Column 23,
Line 41, replace "in vacuo" with italicized word -- in vacuo --.
Lines 60 and 65, replace "cis" with italicized word -- cis --.

Column 24,
Lines 19, 24, 31, 33 and 59, replace "cis" with italicized word -- cis --.

UNITED STATES PATENT AND TRADEMARK OFFICE
CERTIFICATE OF CORRECTION

PATENT NO. : 6,579,986 B2
DATED : June 17, 2003
INVENTOR(S) : Michael S. Allen et al.

It is certified that error appears in the above-identified patent and that said Letters Patent is hereby corrected as shown below:

<u>Column 37,</u>
Line 44, replace "was; worked" with -- was worked --.

<u>Column 38,</u>
Line 25, replace "in-vacuo" with italicized word -- in-vacuo --.

Signed and Sealed this

Sixteenth Day of March, 2004

JON W. DUDAS
*Acting Director of the United States Patent and Trademark Office*